US009542511B2

(12) United States Patent
Chen et al.

(10) Patent No.: US 9,542,511 B2
(45) Date of Patent: Jan. 10, 2017

(54) SYNTHETIC GAS-OIL-RATIO DETERMINATION FOR GAS DOMINANT FLUIDS

(71) Applicant: Halliburton Energy Services, Inc., Houston, TX (US)

(72) Inventors: Dingding Chen, Tomball, TX (US); David L. Perkins, The Woodlands, TX (US); Christopher Michael Jones, Houston, TX (US); Jing Shen, Houston, TX (US); Michael T. Pelletier, Houston, TX (US); Robert Atkinson, Conroe, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 7 days.

(21) Appl. No.: 14/650,820

(22) PCT Filed: Dec. 27, 2013

(86) PCT No.: PCT/US2013/078002
§ 371 (c)(1),
(2) Date: Jun. 9, 2015

(87) PCT Pub. No.: WO2015/099766
PCT Pub. Date: Jul. 2, 2015

(65) Prior Publication Data
US 2016/0283615 A1    Sep. 29, 2016

(51) Int. Cl.
*G06G 7/48* (2006.01)
*G06F 17/50* (2006.01)
*G06F 17/11* (2006.01)
*G06N 3/12* (2006.01)
*G06N 3/04* (2006.01)
*E21B 49/10* (2006.01)

(52) U.S. Cl.
CPC ............ *G06F 17/5009* (2013.01); *E21B 49/10* (2013.01); *G06F 17/11* (2013.01); *G06N 3/0481* (2013.01); *G06N 3/126* (2013.01); *G06F 2217/16* (2013.01)

(58) Field of Classification Search
CPC .......... E21B 49/10; E21B 49/00; E21B 43/00; E21B 49/082; G01N 30/88
See application file for complete search history.

(56) References Cited

U.S. PATENT DOCUMENTS

| 6,236,894 B1 | 5/2001 | Stoisits et al. |
| 2004/0193375 A1 | 9/2004 | Dong et al. |

(Continued)

FOREIGN PATENT DOCUMENTS

| EP | 2416153 | 2/2012 |
| WO | 2012080993 | 6/2012 |

OTHER PUBLICATIONS

Jones et al., "Laboratory quality optical analysis in harsh environments", SPE 163289, Dec. 2012.*

(Continued)

*Primary Examiner* — Kandasamy Thangavelu
(74) *Attorney, Agent, or Firm* — Chamberlain Hrdlicka

(57) ABSTRACT

The disclosed embodiments include a method, apparatus, and computer program product for determining a synthetic gas-oil-ratio for a gas dominant fluid. For example, one disclosed embodiment includes a system that includes at least one processor, and at least one memory coupled to the at least one processor and storing instructions that when executed by the at least one processor performs operations that include optimizing a gas-oil-ratio database using a genetic algorithm and a multivariate regression simulator and generating a synthetic gas-oil-ratio for a gas dominant fluid. In one embodiment, optimizing a gas-oil-ratio database using a genetic algorithm and a multivariate regression simulator comprises defining gas-oil-ratio searching boundaries gas-oil-ratio for each gas dominant fluid; assigning randomly a synthetic gas-oil-ratio for each gas dominant (Continued)

fluid in a set of gas dominant fluids in the initial population of gas-oil-ratio data, wherein the gas-oil-ratio for each gas dominant fluid is within the searching boundaries; generating an initial population of gas-oil-ratio data for a set of gas dominant fluids; and evaluating synthetic gas-oil-ratio assignments for the initial population using the multivariate regression simulator.

20 Claims, 9 Drawing Sheets

(56) References Cited

U.S. PATENT DOCUMENTS

| | | | | |
|---|---|---|---|---|
| 2004/0216521 | A1* | 11/2004 | Shammai | E21B 49/082 73/152.55 |
| 2005/0194131 | A1 | 9/2005 | Tseytlin | |
| 2008/0156486 | A1* | 7/2008 | Ciglenec | E21B 49/10 166/250.15 |
| 2009/0192768 | A1 | 7/2009 | Zuo et al. | |
| 2009/0289628 | A1 | 11/2009 | Minh | |
| 2010/0299111 | A1* | 11/2010 | Dale | E21B 49/00 703/2 |
| 2011/0011595 | A1* | 1/2011 | Huang | E21B 43/00 166/369 |
| 2011/0023583 | A1* | 2/2011 | Jones | G01N 30/88 73/31.05 |
| 2011/0088895 | A1 | 4/2011 | Pop et al. | |

OTHER PUBLICATIONS

Adeyemi et al., "Enhancing oil recovery through high level data mining technology", SPE 164761, Apr. 2013.*
International Search Report and Written Opinion of PCT Application No. PCT/US2013/078002 dated Sep. 22, 2014: pp. 1-10.

* cited by examiner

SYNTHETIC GAS-OIL-RATIO DETERMINATION FOR GAS DOMINANT FLUIDS

BACKGROUND OF THE INVENTION

Gas-Oil-Ratio (GOR) is the ratio of natural gas compared to oil for a particular fluid under certain pressure, volume, and temperature conditions. GOR is an important parameter used for downhole fluid analysis and is used in conjunction with other chemical and physical parameters to characterize the formation fluid properties. In some instances, directly measured GOR data is not obtainable; therefore, real-time software is used to predict a particular fluid GOR from measurements obtained from a particular downhole optical tool during formation testing.

BRIEF DESCRIPTION OF THE DRAWINGS

Illustrative embodiments of the present invention are described in detail below with reference to the attached drawing figures, which are incorporated by reference herein and wherein.

DETAILED DESCRIPTION

Figure 1:
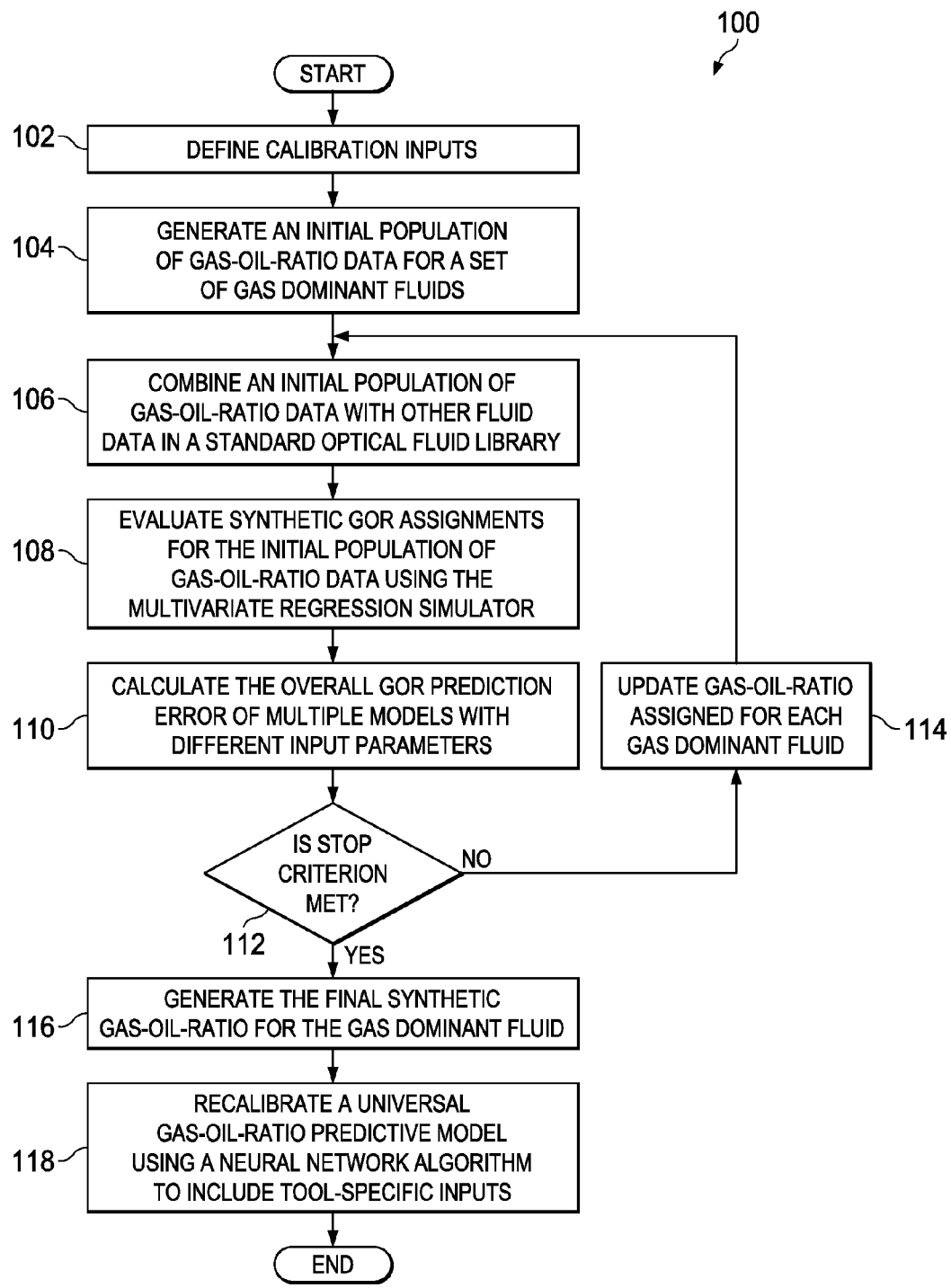
FIG. 1 is a flowchart illustrating an example of a computer implemented method for determining a synthetic GOR for a gas dominant fluid in accordance with the disclosed embodiments.

Conventional predictive modeling of Gas-Oil-Ratios (GORs) is constructed using linear or non-linear regression analysis based on fluids selected from a standard optical fluid library. The standard optical fluid library may include measured and synthetic, or simulated, GORs. Each fluid within the standard optical fluid database may comprise a single fluid, may be a combination of one or more fluids, or may include one or more gases. Each of these fluids within the standard optical fluid library has an associated GOR. However, for gas dominant GORs, or GORs for fluids primarily composed of gas, the actual values are often unknown or hard to determine. Moreover, a pure gas GOR is theoretically infinity, thereby making calibration model development and predictions of GORs for such fluids difficult and interpretation of field data challenging.

The disclosed embodiments provide an approach to determine the synthetic GOR for gas dominant fluids. For example, the synthetic GOR values can be iteratively assigned or estimated through an Evolutionary Optimization process to improve various GOR model predictions over the combined database of global fluid samples such as light oil, medium and heavy oil, live gas and oil condensates, water and gas. The GOR predictive models can be implemented with a variety of algorithms, such as a Partial-Least-Square (PLS) algorithm and Neural Networks. The input parameters for various GOR predictive models may include fluid compositional concentrations, multi-channel optical sensor responses, and any combination of above.

The disclosed methods and systems may be used to determine a synthetic GOR for gas dominant fluids in standard optical fluid libraries. However, it should be appreciated that the disclosed embodiments may also be applied in other industries which may include other hard-to-measure parameters in a database, particularly if the parameter has a high level of uncertainty.

The disclosed embodiments and additional advantages thereof are best understood by referring to FIGS. 1-10 of the drawings, which are appended at the end of this document, like numerals being used for like and corresponding parts of the various drawings. Other features and advantages of the disclosed embodiments will be or will become apparent to one of ordinary skill in the art upon examination of the following figures and detailed description. It is intended that all such additional features and advantages be included within the scope of the disclosed embodiments. Further, the illustrated figures are only exemplary and are not intended to assert or imply any limitation with regard to the environment, architecture, design, or process in which different embodiments may be implemented.

As used herein, the singular forms "a", "an" and "the" are intended to include the plural forms as well, unless the context clearly indicates otherwise. It will be further understood that the terms "comprise" and/or "comprising," when used in this specification and/or the claims, specify the presence of stated features, integers, steps, operations, elements, and/or components, but do not preclude the presence or addition of one or more other features, integers, steps, operations, elements, components, and/or groups thereof. The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. The embodiments were chosen and described to explain the principles of the invention and the practical application, and to enable others of ordinary skill in the art to understand the claimed inventions.

Beginning with FIG. 1, a process 100 is illustrated for determining a synthetic GOR for a gas dominant fluid in accordance with the disclosed embodiments. The determined synthetic GOR may be applied to a universal GOR predictive model which will be applicable to global fluid samples and not limited only to gas-dominant fluids. In this embodiment, a global fluid sample may be any fluid sample for which a calibration analysis may be performed and included in a database for which GOR model predictions will be evaluated.

In general, process 100 utilizes a genetic algorithm and a multivariate regression simulator to optimize synthetic GOR assignments for a gas dominant fluid. Process 100 begins with step 102 by defining calibration inputs which will be used to calculate GORs for global fluid samples. In one embodiment, the calibration inputs are defined by the information provided within a standard optical fluid library and the defined searching boundaries. The standard optical fluid library generally maintains an absorption spectral database of global fluid samples in the visible to near-infrared (NIR) region. The fluid absorption spectral database can be used to simulate optical sensor response when a sensor output transfer function is given. In one embodiment, the simulated sensor responses on the selected fluid samples are used as candidate inputs for generating predictive models. In some embodiments, the standard optical fluid library may comprise fluid information describing the characteristics and properties of the particular fluid. For example, the standard optical fluid library may include fluid constituent properties or parameters, such as chemical concentrations, physical properties, and measured fluid GORs under different pressure/volume/temperature (PVT) conditions. In certain embodiments, it may be beneficial to use the fluid constituent properties or parameters as calibration inputs for GOR prediction because conventional GOR calculation in a laboratory environment is based on the fluid hydrocarbon composition of methane (C1), ethane (C2), propane to pentane (C3-C5), hexane and heavier hydrocarbons. The standard optical fluid library may include any combination and may comprise more or less fluid information than described in the previous examples.

Each fluid within the standard optical fluid database may comprise a single fluid, may be a combination of one or more fluids, or may also include one or more gases. The fraction of each fluid or gas within a single GOR within the standard optical fluid library may vary. In certain instances, for a gas dominant fluid, a GOR may not be included in the standard optical fluid library. Therefore, in accordance with the disclosed embodiments, a synthetic GOR may need to be modeled, predicted, and generated using the data from the standard optical fluid library as well as an optimization routine.

For example, in one embodiment, to develop the optimization routine, searching boundaries setting the range, the minimum, and the maximum GOR for each gas dominant fluid needs to be defined to assist in determining the synthetic GOR for the gas dominant fluid. Such boundaries may be used to limit the range of possible GORs associated with each gas and may be based on generally known searching ranges for downhole fluids, with the maximum boundary set in the tens of thousands. For example, a searching range may be set from 0 to 32767, with the maximum GOR represented by a 15 bit binary string ($2^{15}$=32768).

Once the calibration inputs are defined in step 102, process 100 proceeds to step 104 to generate an initial population of GOR estimations or realizations for a set of gas dominant fluids. In one embodiment, one or more gas dominant fluids are selected from all the gas dominant fluids from which a synthetic GOR is to be determined. The selected gas dominant fluids form the set of gas dominant fluids. GORs for each selected gas dominant fluid is randomly assigned a GOR within the searching boundaries defined in step 102. The assigned GOR estimations or realizations in the initial population will be used as the training targets or true values for the calibration analysis further explained below.

In step 106 of process 100, measured GORs from other fluid samples in the standard optical fluid library are combined with each realization of the initial population of GOR data in step 104 to form data sets of target GORs for calibration analysis, or GOR calibration data sets. In one embodiment, the target GORs will be used as calibration outputs for performing standard regression analysis as further described below. As indicated above in step 104, the calibration inputs will be the known fluid properties and optical characteristics measured or simulated on the same fluid samples from the standard optical fluid library. For example, in one embodiment, the set of GOR calibration inputs may include only fluid constituent concentrations. In another embodiment, the set of GOR calibration inputs may include only optical sensor responses simulated on the same fluids. Still, in another embodiment, the set of GOR calibration inputs might be the combination of above.

After GOR calibration data sets are formed in step 106, process 100 continues step 108 process 100 proceeds to evaluate synthetic GOR assignments for gas dominant fluids from step 104 using a multivariate regression simulator. In some embodiments, a multivariate regression simulator may be implemented with any type of linear regression algorithm, such as a Partial-Least-Square (PLS) algorithm or Principal Component Analysis (PCA) using multiple inputs and single output.

In step 108, in one embodiment, a PLS algorithm is performed as a fast regression routine to determine the best linear correlation coefficients for GOR prediction. A multi-objective function is applied to each individual realization generated in step 104 to determine a respective performance measure or cost function. In one embodiment, the multi-objective function is a cost function as illustrated by Equation (1):

$$F = L_1 \times SEC_1 + L_2 \times SEC_2 + L_3 \times SEC_3$$

where $L_1$, $L_2$ and $L_3$ are weighting coefficients. In one embodiment, $SEC_1$ is the standard error of the GOR prediction calculated with a model using the fluid chemical concentrations and physical properties as inputs; $SEC_2$ is calculated with a model using optical sensor responses as inputs; and $SEC_3$ is calculated with a model using some combinational inputs of above.

In some embodiments, the standard error of calibration (SEC) for each $SEC_N$ in Equation (1) is the relative error of calibration over three discrete groups of fluids having three distinct GOR ranges: (1) GOR<=2000 (e.g., a fluid composed of low GOR oil and a water/brine combination); (2) 2000<GOR<=7000 (e.g., a fluid composed of medium GOR live oil condensates); and (3) GOR>7000 (e.g., a fluid comprising high GOR gas-dominant fluids).

The three distinct GOR ranges may be a standard set of ranges or a customized range set of ranges. The relative error of calibration for the three aforementioned distinct GOR ranges may be expressed using Equation (2):

$$SEC = K_1 \frac{RMS_1 \times 2 \times 100}{MIN(GOR_1) + MAX(GOR_1)} +$$

$$K_2 \frac{\text{RMS}_2 \times 2 \times 100}{\text{MIN}(GOR_2) + \text{MAX}(GOR_2)} + K_3 \frac{\text{RMS}_3 \times 2 \times 100}{\text{MIN}(GOR_3) + \text{MAX}(GOR_3)}$$

where $K_1$, $K_2$ and $K_3$ are weighting coefficients; and $RMS_1$ and $GOR_1$, $RMS_2$ and $GOR_2$ and $RMS_3$ and $GOR_3$ are respectively root mean-squared error and target GOR values in each distinct group. In one embodiment, $K_1=\frac{1}{3}$, $K_2=\frac{1}{3}$ and $K_3=\frac{1}{3}$ may be used. In other embodiments, the values of $K_1$, $K_2$ and $K_3$ may be dependent on other requirements, such as prediction requirements associated with each distinct group.

In some embodiments, the cost function, illustrated by Equation (1), may also include other components. For example, Equation (1) may include the difference of SECs and the standard deviation between the missing data model (i.e., a gas-exclusive model) and the complete-data model (i.e., a gas-inclusive model). In some embodiments, the missing data model is a set of incomplete multivariate data which assumes that GORs for gas fluids is missing. In some embodiments, a multiple imputation method is used to solve the incomplete data by repeatedly solving the complete data version. In some embodiments, a Monte Carlo method may be used to replace the incomplete data, and an Expectation Maximization algorithm or a Bayesian posterior estimation algorithm may be used to optimize the resulting data set to determine the maximum likelihood and accuracy of the resulting data set. Thus, for example, Equation (1) may include the difference of SEC's and the standard deviation to account for these embodiments.

After the multivariate regression simulator is applied, process 100 proceeds to step 110 where the overall GOR prediction error for multiple models having different input parameters is calculated. In one embodiment, process 100 continues to decision step 112 to determine whether a stop criterion is met. In one embodiment, the stop criterion is met when one of a pre-determined threshold of a cost function determined in step 108 occurs or a maximum number of generations or iterations performed by a genetic algorithm as further described below occurs.

For instance, in one embodiment, to determine whether a stop criterion is met, each cost function calculated in step 108 is ranked against the other cost functions for each individual realization. In some embodiments, the cost function for each realization in the training set is ranked based on the GOR prediction error calculated on all selected fluid samples under calibration, including gas-dominant samples and other fluid samples such as light oils, medium to heavy oils and water.

If the stop criterion is not met such that the cost function is not minimized to the pre-determined threshold or maximum number of iteration is not reached ("no" answer to decision step 112), then process 100 proceeds to step 114 and updates the GOR assigned to each gas dominant fluid so that the optimization loop (steps 106 through 114) is initialized to minimize the cost function using a genetic algorithm. A genetic algorithm, such as an Evolutionary Computation or computational intelligent algorithm, employs a continuous optimization model that utilizes an iterative process to mimic the metaphor of natural biologic evolution. Genetic algorithms operate on a population of potential solutions and apply the principle of survival of the fittest to produce improved solutions through multiple generations. At each generation, the fitness of each individual is evaluated based on the user-defined objective function, and an updated population of solutions are created by using genetic operators such as ranking, selection, crossover and mutation.

For example, in one embodiment, genetic operators are applied to the ranked cost functions for each realization in the initial population of GOR estimations, and the GOR assigned for each gas dominant fluid is updated at step 114. More specifically, the GOR assigned to the initial population of GOR data for gas dominant fluids in step 102 is updated with new GOR assignments. For example, the Evolutionary Computation algorithm applies the at least one process of selection, crossover, and mutation to update the GOR assigned for each gas dominant fluid. After updated GORs are assigned, process 100 returns to step 106 so that the updated GORs in the initial population of GOR data are combined with the set of data from the standard optical fluid library. The optimization loop may be repeated a number of times so that multiple generations of calculations using the genetic operators are completed until the stop criterion is met.

If the stop criterion is met ("yes" answer to decision step 112), process 100 proceeds to step 116 to output or generate the final synthetic GOR for the gas dominant fluid based on the optimization routine performed. In accordance with the disclosed embodiments, the generated synthetic gas-dominant GOR values may be used as "true" values for the corresponding fluids and form the subset of training data in developing a universal GOR predictive model that may be optical tool dependent. In one embodiment, process 100 utilizes all available and useful parameters in the standard optical fluid library as candidate inputs to optimize the gas-dominant GOR assessment. However, such inputs, particularly the fluid constituent concentrations, may not always be obtainable in downhole measurements using the optical tools currently available. Therefore, some of the input parameters used to determine the synthetic GOR for the gas dominant fluid may need to be adjusted for developing optical tool-specific universal GOR predictive models. For example, in some embodiments, the inputs used in step 108 may need to be adjusted or recalibrated to include only the obtainable input parameters.

Thus, in some embodiments, process 100 may optionally proceed to step 118 so that a universal GOR predictive model is robustly recalibrated using a non-linear artificial neural network algorithm to include tool-specific inputs. An artificial neural network algorithm, also known as neural network algorithm, is a predictive modeling tool and computational model that identifies patterns within a set of data and is able to improve or apply new information to the set of data. Thus, through recalibration with neural network algorithm, process 100 may generate a gas-inclusive universal GOR predictive model using the results provided at step 116 that may include obtainable inputs by a specific measurement tool to be used in field data processing.

Figure 2:
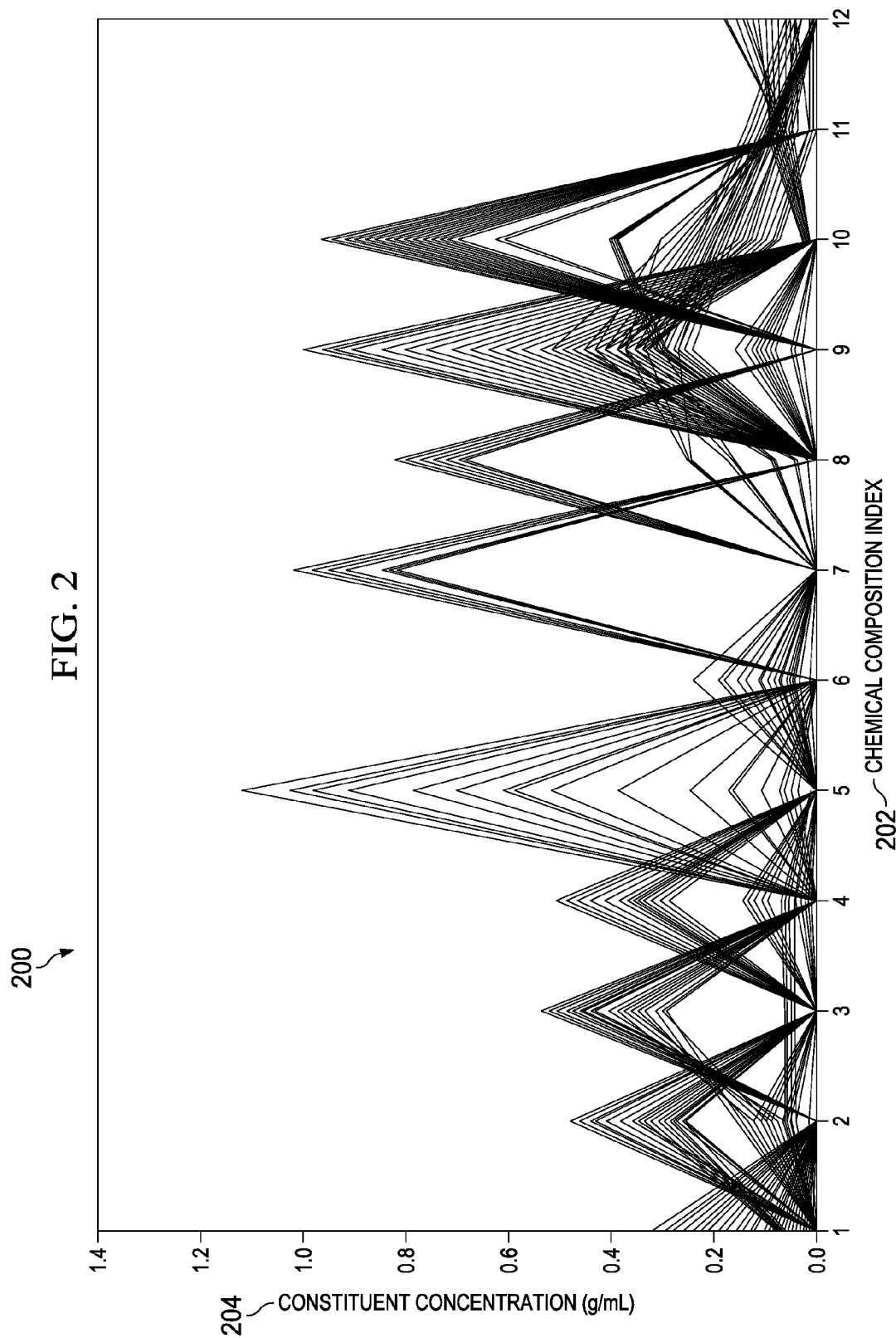
FIG. 2 is a graph illustrating an example data range of 12 major chemical concentrations measured on fluids under different temperature and pressure combinations in accordance with the disclosed embodiments.

With reference now to FIG. 2, a graph depicting a data range of twelve (12) major chemical concentrations measured on fluid samples under different temperature and pressure combinations is presented in accordance with the disclosed embodiments. Data range 200 may be combined with the initial population of GOR data as indicated in step 106 of FIG. 1. In this embodiment, data range 200 shows constituent concentrations of fifty (50) fluid samples under different temperature and pressure combinations. Chemical composition index 202 identifies twelve (12) distinct chemicals for which constituent concentration levels 204 correspond. In this embodiment, the twelve distinct chemical composition index 202 numbers correspond with the following chemicals:

| 1 | Methane |
| --- | --- |
| 2 | Ethane |
| 3 | Propane |
| 4 | Butane and Pentane |
| 5 | $CO_2$ |
| 6 | $N_2$ |
| 7 | $H_2O$ |
| 8 | Ester and Olefin |
| 9 | Saturates |
| 10 | Aromatics |
| 11 | Resins |
| 12 | Asphaltenes |

The concentration of each chemical within each of the 50 fluid samples is reflected in data range 200.

In some embodiments, the data within optical fluid library may include other information describing the characteristics, properties, and attributes of the particular fluids within the optical fluid library. Such information may include the chemical properties, physical properties, or the measured fluid GORs under different pressures and temperatures. As described above in reference to process 100, this information may be provided as a calibration input. It should be understood by those of ordinary skill in the art that data range 200 is exemplary and may include more or less fluid samples and different types of chemicals or fluids than illustrated by FIG. 2.

Figure 3:
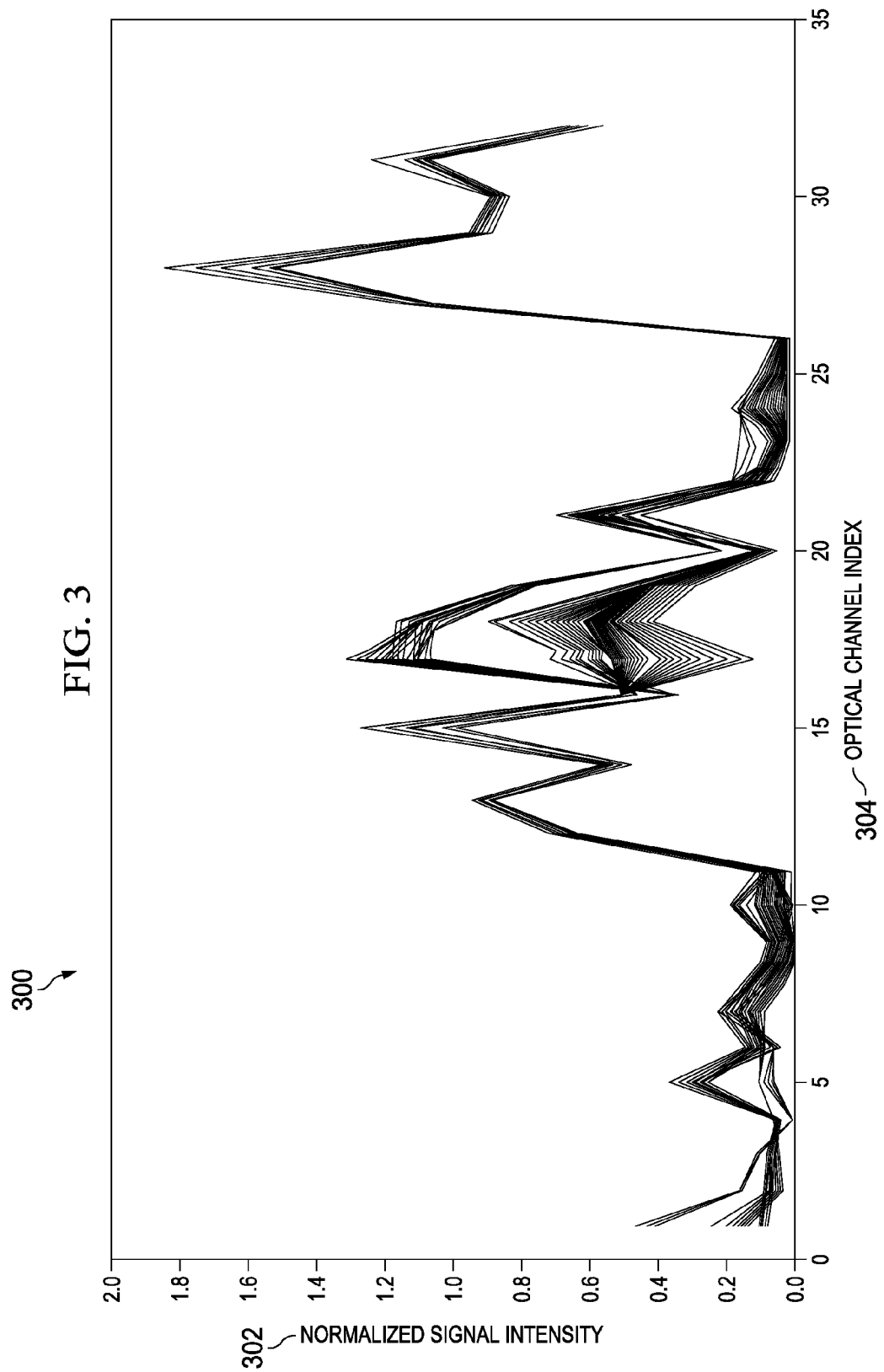
FIG. 3 is a graph illustrating an example data range of normalized optical signal responses on 32 channels associated with different optical elements in accordance with the disclosed embodiments.

As an example, FIG. 3 depicts a data range of normalized optical signal responses on 32 channels associated with different optical elements in accordance with the disclosed embodiments. Data range 300 may be combined with the initial population of GOR data as indicated in step 106 of FIG. 1 or may be used in step 118 of FIG. 1 to recalibrate data for measurement tool-specific inputs. In this embodiment, data range 300 illustrates synthetic multi-channel optical sensor responses for each fluid which is measurement tool dependent under similar test conditions. Normalized Signal Intensity 302 is the data range of normalized optical signal responses across different Optical Channel Index 304. In data range 300, each of the 32 indices for Optical Channel Index 304 represents a different optical element corresponding to a particular set of characteristics or a defined band or filter. For example, one index may correspond with an integrated computation element (also known as an ICE Core element), an optical component encoded with pre-designed multivariate regression vectors for various properties of interest. As another example, the index may correspond to a narrowband set of filters. It should be understood by those of ordinary skill in the art that data range 300 is exemplary and may include more or less indices or channels than illustrated by FIG. 3.

Figure 4:
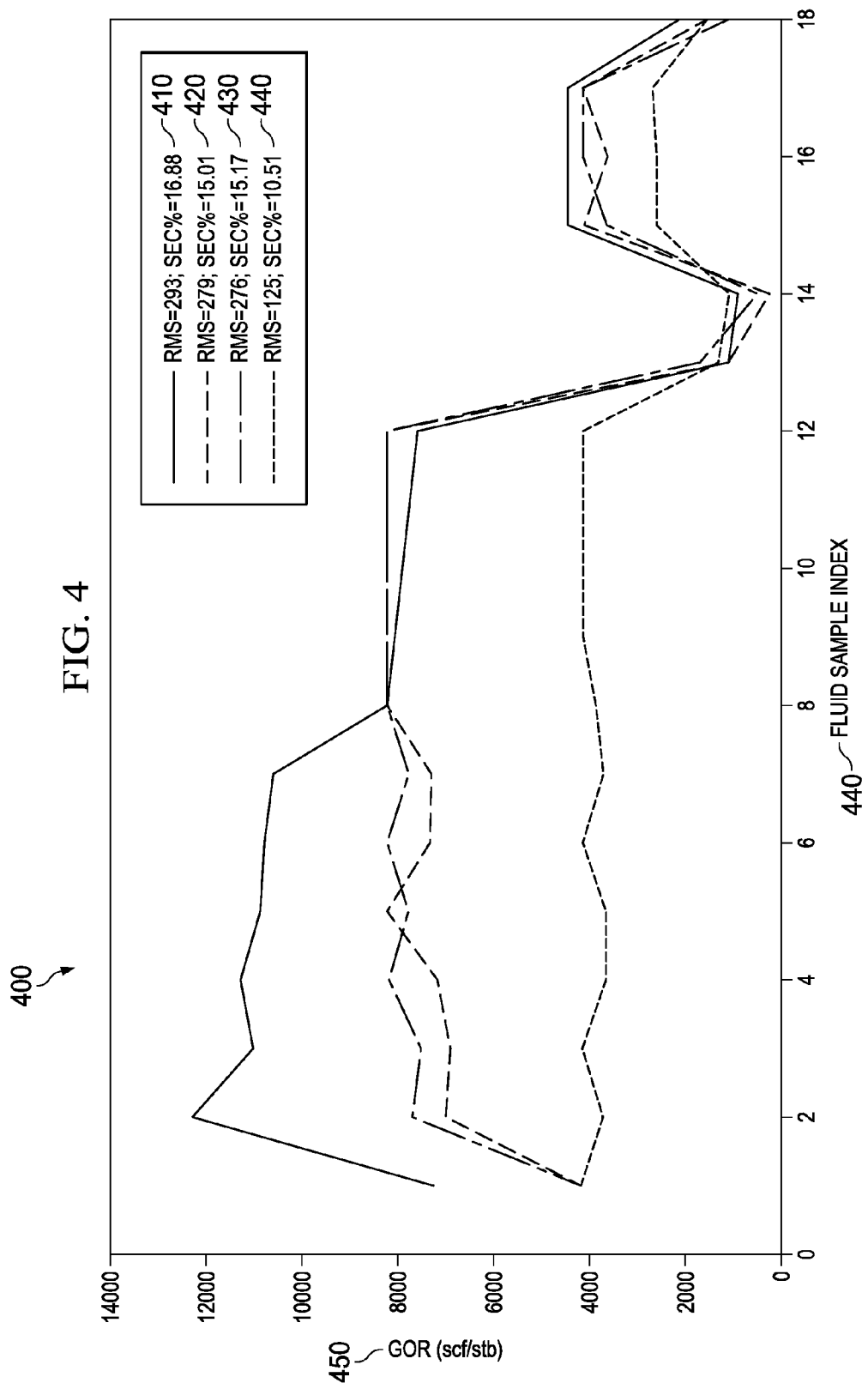
FIG. 4 is a graph illustrating an example of simulation results for synthetic GORs generated in accordance with the disclosed embodiments.

FIG. 4 is a graph illustrating an example of simulation results for synthetic GORs generated in accordance with the disclosed embodiments. In this embodiment, graph 400 depicts simulation results for four different simulation runs, namely, runs 410, 420, 430, and 440. A root-mean-square (RMS) error and a standard error of calibration (SEC) are associated with each of runs 410 through 440. Fluid Sample Index 440 identifies eighteen (18) different fluid samples of gas dominant fluids. In this embodiment, the eighteen Fluid Sample Index 440 numbers correspond with the following fluid samples:

| 1 | Methane |
| --- | --- |
| 2-7 | Propane + Ethane, Methane, and water |
| 8-12 | Ethane + Methane and saturates |
| 13 | $CO_2$ |
| 14 | $N_2$ |
| 15-18 | Live gas/oil condensates |

GOR 450 is the synthetic GOR generated for each fluid sample with Fluid Sample Index 440 within each of runs 410 through 440. In some embodiments, GOR 450 is measured in standard cubic feet (scf) per standard barrel (stb) of liquid.

The determination of a synthetic GOR for gas dominant fluids is an extrapolation problem due to an extremely large variation in dynamic range in GOR that is beyond the limit of GOR values for other fluids, thereby yielding multiple solutions by applying different constraints, such as searching range and model input selection. For example, run 440 is a less constrained model having a wide searching range and a low synthetic GOR around 4000 scf/stb as output for Fluid Sample Indices 1 through 12. On the other hand, run 410 is a more constrained model having a narrow searching range and a diverse range of GOR values as output. Although run 410 also has a larger calibration error (RMS=293; SEC %=16.88) using a linear model, run 410 may be a more practical realization or generation of synthetic GOR values for the gas dominant fluids.

Figure 5:
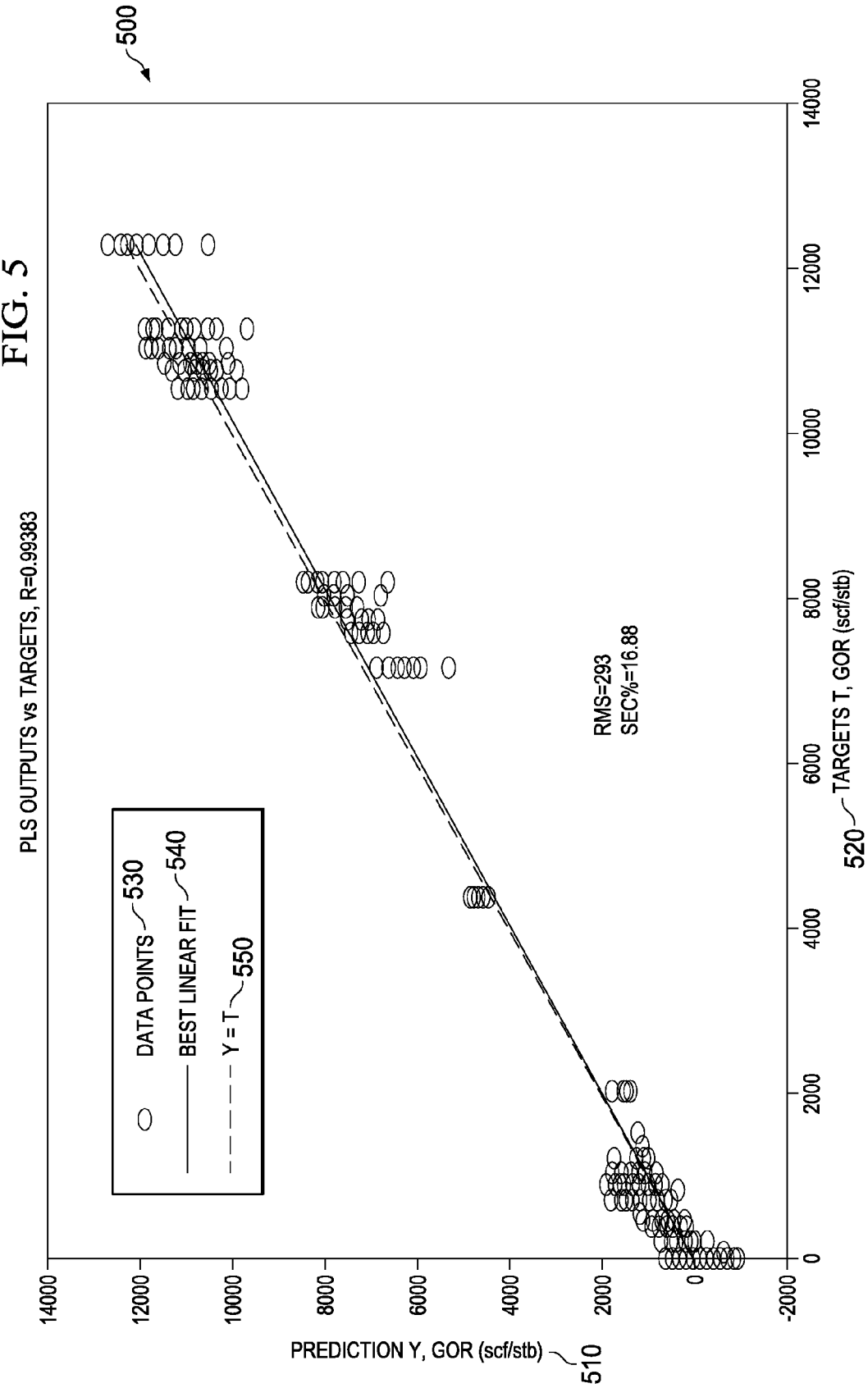
FIG. 5 is an exemplary graph comparing the simulation results of FIG. 4 against target GOR values for the same fluids in accordance with the disclosed embodiments.

With reference to FIG. 5, a graph 500 is presented that compares the results of the GOR prediction run 410 of FIG. 4 against target GOR values for the same fluids (including synthetic GORs for gas dominant samples) that are determined in accordance with the disclosed embodiments. Prediction Y 510 depicts the calculated GOR for diverse fluids using a PLS model in accordance with the disclosed embodiments. In this embodiment, chemical property inputs and measured optical signal responses in a standard optical fluid library, as indicated in step 102 of FIG. 1, are used. Targets T 520 shows target GOR values for the respective fluids. Each of data points 530 is a separate point of GOR prediction against its target value. Best linear fit 540 illustrates the line which is the best linear fit for all of data points 530, and Y=T line 550 illustrates the line if all GORs calculated using a PLS model matched or were exactly the same as the target GOR values.

In the depicted embodiment, graph 500 indicates that, even by including GOR predictions with a PLS model calibrated with gas-inclusive GORs, fluid samples using chemical and optical inputs are highly correlated to target GOR values for the respective fluids, namely the respective fluids have a correlation coefficient of 0.9938. Linear GOR modeling such as PLS calibration may have problems in dealing with large dynamic range in parameter space over different fluids using a single universal model. By properly assigning synthetic GOR values on gas dominant fluids in accordance with disclosed embodiment during calibration, it is possible to achieve the consistent quality of predictions over the wide GOR range associated with diverse fluids as shown in graph 500.

Figure 6:
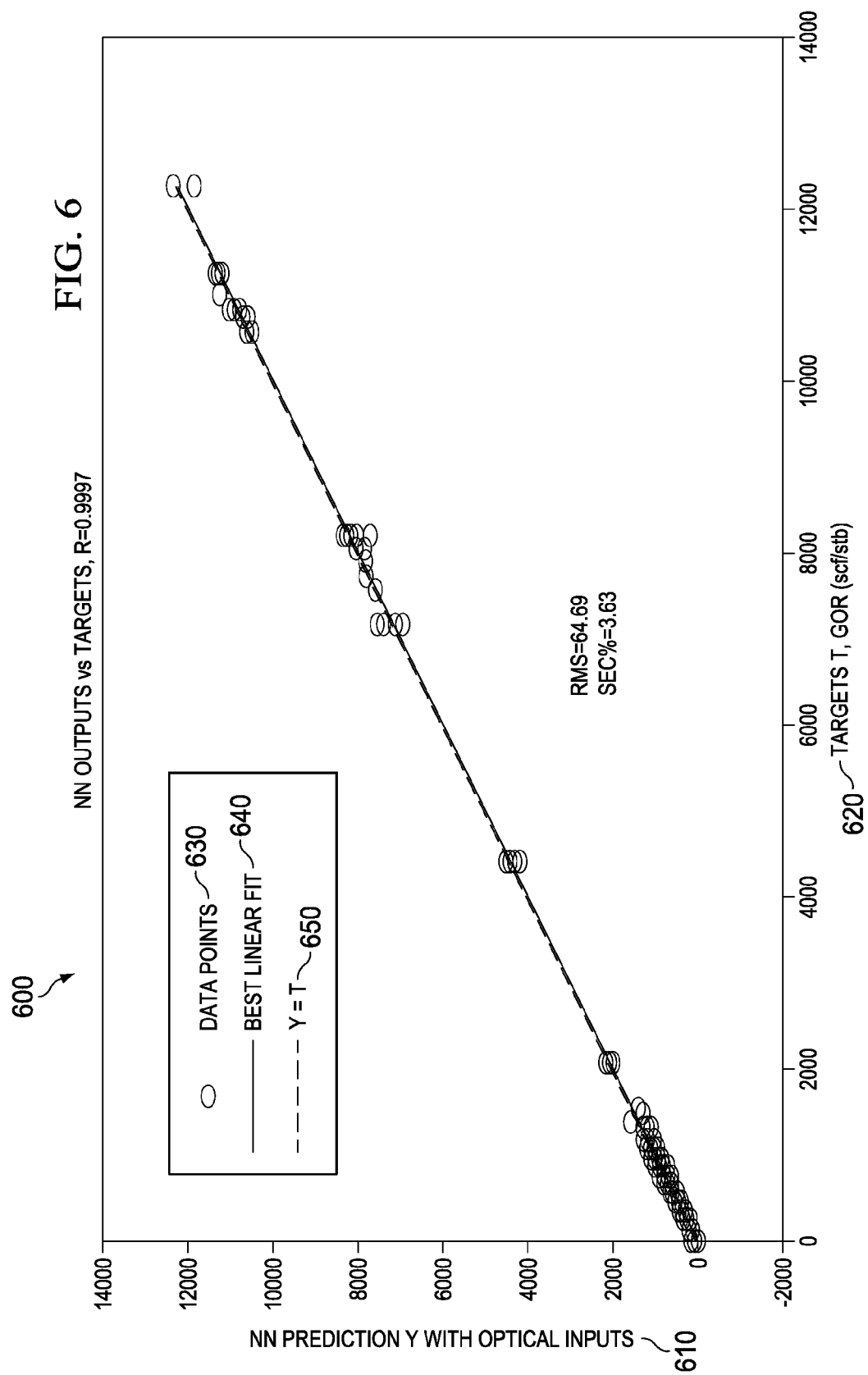
FIG. 6 is an exemplary graph comparing prediction of GORs using a neural network algorithm against target GOR values for the respective fluids illustrated in FIG. 5, in accordance with disclosed embodiments.

FIG. 6 is an exemplary graph comparing prediction of GORs using a neural network algorithm against target GOR values for the respective fluids illustrated in FIG. 5, in accordance with disclosed embodiments. In some embodiments, generated synthetic GORs for gas dominant fluids are combined with available GORs in a standard optical fluid library for other fluids and recalibrated using an artificial neural network algorithm, as exemplified in step 118 of FIG. 1. Graph 600 shows NN Prediction Y 610 representing the GOR for various fluids after a neural network (NN) algorithm is applied. In this embodiment, 12 optical signal responses can be obtained from measurements of downhole measurement tools, and, thus, an NN algorithm can be applied to those 12 optical signal responses. Targets T 620 is similar to Targets T 520 of FIG. 5, which shows the "true" GOR values for various fluids in a combined database comprising synthetic high GORs for gas dominant fluids, in accordance with the disclosed embodiments, and measured low to medium GORs for other fluids. Each of data points 630 is the point of predicted value with NN model against its target. Best linear fit 640 illustrates the line which is the best linear fit for all of data points 630, and Y=T line 650 illustrates the line if all GORs calculated using a NN algorithm matched or were exactly the same as the target GOR values for the respective fluids.

In this embodiment, graph 600 shows that GORs recalibrated using an NN algorithm are much closer to target GOR values than those using a PLS model as seen in graph 500 of FIG. 5. Since NN algorithm is capable of tackling non-linear factors associated with both inputs and outputs of the training data set, it can be effectively used to finalize GOR calibration model, especially when relationship between calibration inputs and outputs, such as optical sensor responses and GOR, appears non-linear in nature. However, neural network model training requires multiple iterations depending on the complexity of problem. For this reason, a fast PLS algorithm in the optimization loop may be used to assess the synthetic GOR values for gas dominant fluids, and NN may be used to finalize all-fluid GOR calibration model after the gas dominant GOR values are determined.

Figure 7:
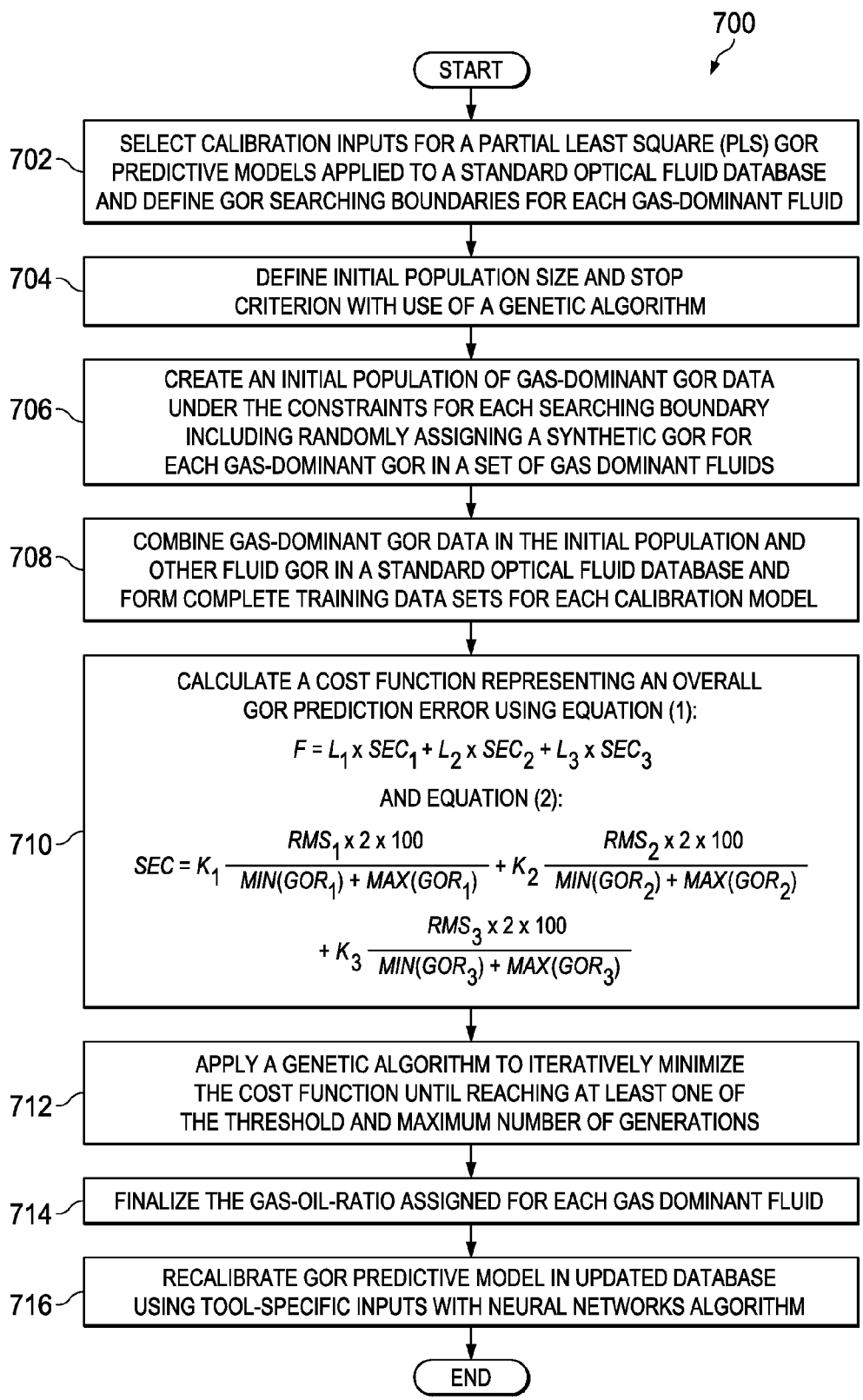
FIG. 7 is a flowchart illustrating another example of a computer implemented method for generating a synthetic GOR for a gas dominant fluid in accordance with the disclosed embodiments.

Referring now to FIG. 7, a flowchart is presented that illustrates an example of a computer implemented method (process 700) for generating a synthetic GOR for a gas dominant fluid in accordance with the disclosed embodiments. The synthetic GOR for the gas dominant fluid may be used in a combined database and may be used to generate values for universal GOR predictive model development in accordance with the disclosed embodiments.

In general, process 700 begins at step 702 by selecting calibration inputs for PLS GOR predictive models which will be applied to a standard optical fluid database and defining GOR searching boundaries for each gas-dominant sample. Process 700 then proceeds to step 704 to define initial population size and stop criterion with use of a genetic algorithm. In step 706, process 700 randomly creates an initial population of gas-dominant GOR data under the constraints for each searching boundary. The initial population includes a set of gas dominant fluids which may have been randomly assigned a synthetic GOR. Thereafter, process 700 proceeds to step 708 whereby gas-dominant GOR data and other fluid GOR in standard optical fluid database are combined to form a complete training data sets for each calibration model. In step 710, a cost function based on a weighted sum of standard calibration errors for the gas-oil-ratio database for each of the set of fluid and selected model inputs is calculated. Specifically, the cost function is illustrated by Equation (1) above and incorporates Equation (2) as the relative error of calibration. A genetic algorithm is applied, in step 712, to iteratively minimize the cost function until reaching at least one the threshold or maximum number of generations. Process 700 proceeds to step 714 to finalize the gas-oil-ratio assigned for each gas dominant fluid. The GOR predictive model in updated database using tool-specific inputs is recalibrated with neural networks in step 716, with process 700 terminating thereafter.

Figure 8:
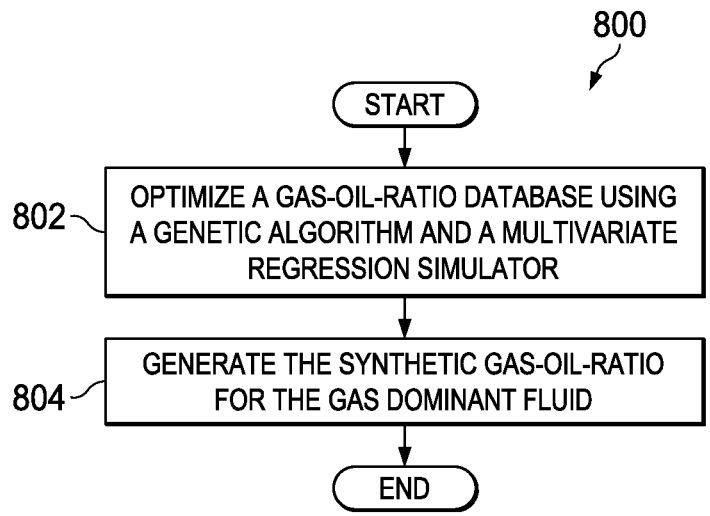
FIG. 8 is a flowchart illustrating an alternative embodiment of a computer implemented method for determining a synthetic GOR for a gas dominant fluid in accordance with the disclosed embodiments.

FIG. 8 is a flowchart illustrating an alternative embodiment of a computer implemented method for determining a synthetic GOR for a gas dominant fluid in accordance with the disclosed embodiments. In FIG. 8, process 800 begins at step 802 by optimizing a GOR database using a genetic algorithm and a multivariate regression simulator. In some embodiments, the GOR database may be a subset of a database of a standard optical fluid library, consisting of available information of global fluid samples for GOR modeling such as the obtainable GOR data for known fluids, high-uncertainty GOR data for gas dominant fluids, and the associated chemical, physical and optical properties for all respective fluids. The GOR database can be updated through synthetic gas dominant GOR optimization by adjusting searching range and minimizing the cost function of variable input calibration models evaluated on combined data set including both gas dominant fluid samples and other fluid samples. The cost function is a multi-objective measurement of weighted sum of relative calibration errors on multiple models with chemical, optical and combinational inputs respectively. The weighting factors of the cost function can be adjusted based on the prior knowledge about the uncertainty of each type of inputs. The GOR database optimization may also include balancing the number of different types of fluids in database to determine the best trade-off in cost function evaluation. Once the GOR database optimization is complete, process 800 proceeds to step 804 so that the synthetic GORs for gas dominant fluids are finalized, the universal GOR predictive model then can be calibrated using all-fluid data for tool-specific application. Process 800 ends thereafter.

Figure 9:
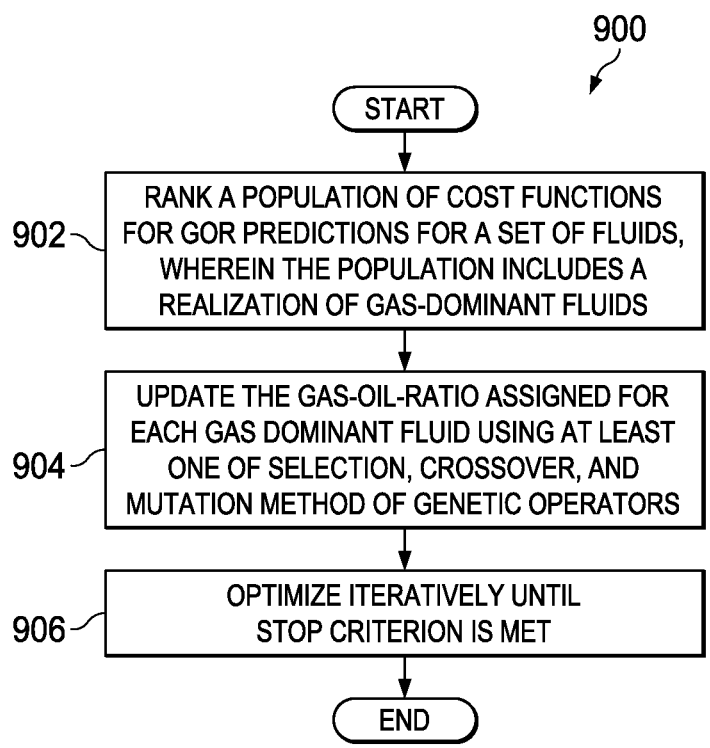
FIG. 9 is a flowchart illustrating an example of a computer implemented method for applying a genetic algorithm in accordance with the disclosed embodiments.

Referring to FIG. 9, process 900 shows a flowchart illustrating an example of a computer implemented method for applying a genetic algorithm in accordance with the disclosed embodiments. Process 900 generally begins with step 902 by ranking a population of cost functions on GOR predictions for all fluids with each initial realization of gas dominant fluids included. In step 904, the assigned GOR for each gas dominant fluid is updated using at least one of a selection, crossover, and mutation method of genetic operators. In some embodiments, multiple generations of calculations using one of the genetic operators may be used. Iterative optimization continues as process 900 proceeds to step 906 until a stop criterion is met, with process 900 terminating thereafter.

Figure 10:
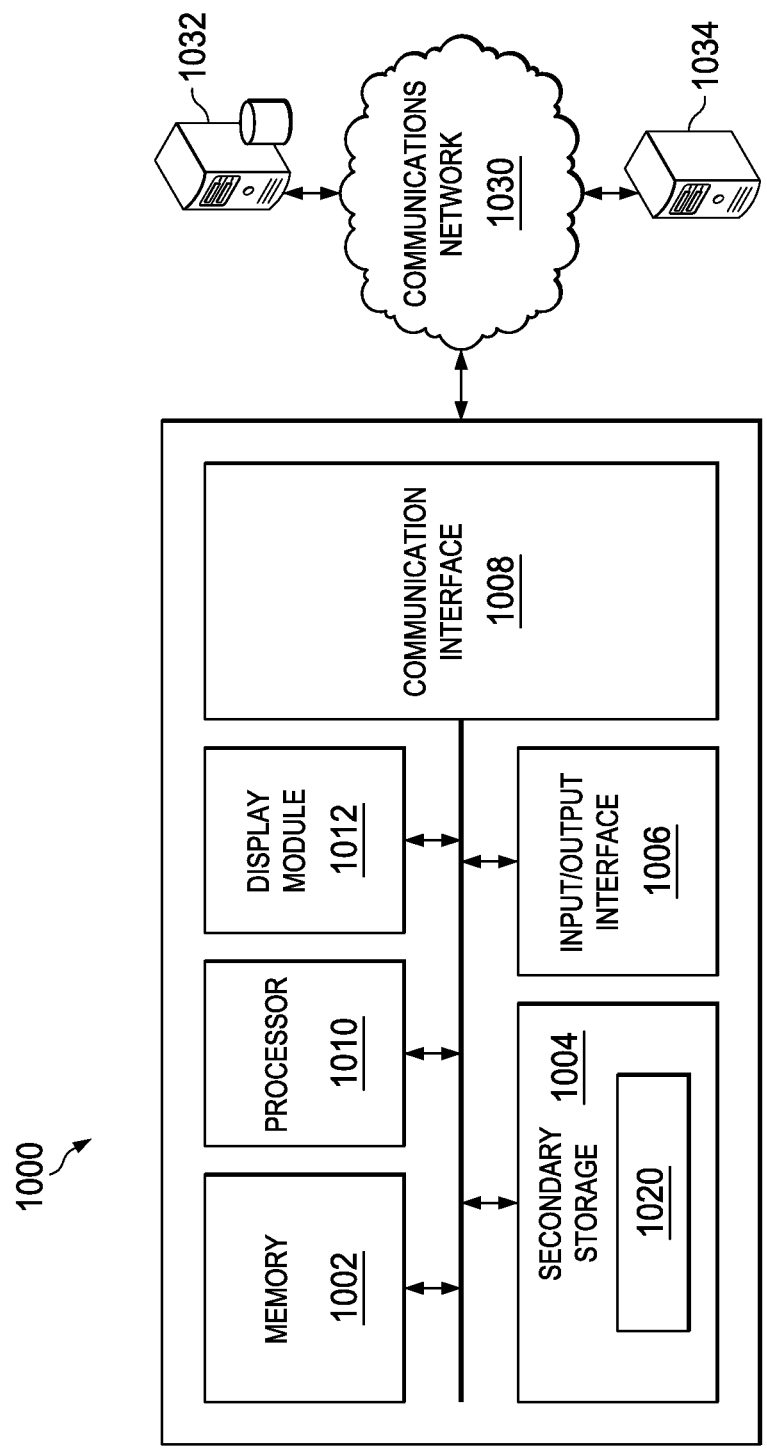
FIG. 10 is a block diagram illustrating one embodiment of a system for implementing the disclosed embodiments.

FIG. 10 is a block diagram illustrating one embodiment of a system 1000 for implementing the features and functions of the disclosed embodiments. Generally, in one embodiment, the system 1000 includes, among other components, a processor 1010, main memory 1002, secondary storage unit 1004, an input/output interface module 1006, and a communication interface module 1008. The processor 1010 may be any type or any number of single core or multi-core processors capable of executing instructions for performing the features and functions of the disclosed embodiments.

The input/output interface module 1006 enables the system 1000 to receive user input (e.g., from a keyboard and mouse) and output information to one or more devices such as, but not limited to, printers, external data storage devices, and audio speakers. The system 1000 may optionally include a separate display module 1012 to enable information to be displayed on an integrated or external display device. For instance, the display module 1012 may include instructions or hardware (e.g., a graphics card or chip) for providing enhanced graphics, touchscreen, and/or multi-touch functionalities associated with one or more display devices.

Main memory 1002 is volatile memory that stores currently executing instructions/data or instructions/data that are prefetched for execution. The secondary storage unit 1004 is non-volatile memory for storing persistent data. The secondary storage unit 1004 may be or include any type of data storage component such as a hard drive, a flash drive, or a memory card. In one embodiment, the secondary storage unit 1004 stores the computer executable code/instructions and other relevant data for enabling a user to perform the features and functions of the disclosed embodiments.

For example, in accordance with the disclosed embodiments, the secondary storage unit 1004 may permanently store the executable code/instructions 1020 for performing the above-described determination of a synthetic GOR for a gas dominant fluid. The executable code/instructions 1020 are then loaded from the secondary storage unit 1004 to main memory 1002 during execution by the processor 1000 for performing the disclosed embodiments.

Additionally, in some embodiments, the system 1000 uses the communication interface module 1008 to communicate with a communications network 1030. For example, the network interface module 1008 may include a network interface card and/or a wireless transceiver for enabling the system 1000 to send and receive data through the communications network 1030 and/or directly with other devices. The communications network 1030 may be any type of network including a combination of one or more of the following networks: a wide area network, a local area network, one or more private networks, the Internet, a telephone network such as the public switched telephone network (PSTN), one or more cellular networks, and wireless data networks. The communications network 1030 may include a plurality of network nodes (not depicted) such as routers, network access points/gateways, switches, DNS servers, proxy servers, and other network nodes for assisting in routing of data/communications between devices.

In some embodiments, the system 1000 may interact with one or more servers 1034 or databases 1032 (e.g., Landmark's Engineer's Data Model™ database) for performing the features of the present invention. For instance, the system 1000 may query the database 1032 to retrieve well data in accordance with the disclosed embodiments.

While specific details about the above embodiments have been described, the above hardware and software descriptions are intended merely as example embodiments and are not intended to limit the structure or implementation of the disclosed embodiments. For instance, although many other internal components of the system 1000 are not shown, those of ordinary skill in the art will appreciate that such components and their interconnection are well known.

In addition, certain aspects of the disclosed embodiments, as outlined above, may be embodied in software that is executed using one or more processing units/components. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives, optical or magnetic disks, and the like, which may provide storage at any time for the software programming.

Additionally, the flowchart and block diagrams in the figures illustrate the architecture, functionality, and operation of possible implementations of systems, methods and computer program products according to various embodiments of the present invention. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In addition to the embodiments described above, many examples of specific combinations are within the scope of the disclosure, some of which are detailed in the below.

Example One

A computer-implemented method for determining a synthetic gas-oil-ratio for a gas dominant fluid, the method comprising optimizing a gas-oil-ratio database using a genetic algorithm and a multivariate regression simulator; and generating the synthetic gas-oil-ratio for the gas dominant fluid.

Example Two

A computer-implemented method for determining a synthetic gas-oil-ratio for a gas dominant fluid, the method comprising optimizing a gas-oil-ratio database using a genetic algorithm and a multivariate regression simulator; and generating the synthetic gas-oil-ratio for the gas dominant fluid, wherein optimizing a gas-oil-ratio database using a genetic algorithm and a multivariate regression simulator comprises defining gas-oil-ratio searching boundaries gas-oil-ratio for each gas dominant fluid; generating an initial population of gas-oil-ratio data for a set of gas dominant fluids; and evaluating synthetic gas-oil-ratio assignments for the initial population using the multivariate regression simulator.

Example Three

A computer-implemented method for determining a synthetic gas-oil-ratio for a gas dominant fluid, the method comprising optimizing a gas-oil-ratio database using a genetic algorithm and a multivariate regression simulator; and generating the synthetic gas-oil-ratio for the gas dominant fluid, wherein optimizing a gas-oil-ratio database using a genetic algorithm and a multivariate regression simulator comprises defining gas-oil-ratio searching boundaries gas-oil-ratio for each gas dominant fluid; generating an initial population of gas-oil-ratio data for a set of gas dominant fluids; and evaluating synthetic gas-oil-ratio assignments for the initial population using the multivariate regression simulator, wherein generating an initial population of gas-oil-ratio data for the gas dominant fluids comprises assigning randomly a synthetic gas-oil-ratio for each gas dominant fluid in a set of gas dominant fluids in the initial population of gas-oil-ratio data, wherein the gas-oil-ratio for each gas dominant fluid is within the searching boundaries.

Example Four

A computer-implemented method for determining a synthetic gas-oil-ratio for a gas dominant fluid, the method comprising optimizing a gas-oil-ratio database using a genetic algorithm and a multivariate regression simulator;

and generating the synthetic gas-oil-ratio for the gas dominant fluid, wherein optimizing a gas-oil-ratio database using a genetic algorithm and a multivariate regression simulator comprises defining gas-oil-ratio searching boundaries gas-oil-ratio for each gas dominant fluid; generating an initial population of gas-oil-ratio data for a set of gas dominant fluids; and evaluating synthetic gas-oil-ratio assignments for the initial population using the multivariate regression simulator, wherein evaluating synthetic gas-oil-ratio assignments for the initial population using the multivariate regression simulator comprises combining the initial population of gas-oil-ratio data for a set of gas dominant fluids and a set of data for other fluids from a standard optical fluid library, wherein the step of combining forms a combined fluid set; and calculating an overall gas-oil-ratio prediction error through a plurality of models having a plurality of inputs.

Example Five

A computer-implemented method for determining a synthetic gas-oil-ratio for a gas dominant fluid, the method comprising optimizing a gas-oil-ratio database using a genetic algorithm and a multivariate regression simulator; and generating the synthetic gas-oil-ratio for the gas dominant fluid, wherein optimizing a gas-oil-ratio database using a genetic algorithm and a multivariate regression simulator comprises defining gas-oil-ratio searching boundaries gas-oil-ratio for each gas dominant fluid; generating an initial population of gas-oil-ratio data for a set of gas dominant fluids; and evaluating synthetic gas-oil-ratio assignments for the initial population using the multivariate regression simulator, wherein evaluating synthetic gas-oil-ratio assignments for the initial population using the multivariate regression simulator comprises combining the initial population of gas-oil-ratio data for a set of gas dominant fluids and a set of data for other fluids from a standard optical fluid library, wherein the step of combining forms a combined fluid set; and calculating an overall gas-oil-ratio prediction error through a plurality of models having a plurality of inputs, wherein the plurality of models comprises at least one of a model comprising fluid chemical concentrations and physical property inputs, a model comprising optical sensor inputs, and a model comprising a combination of the model comprising fluid chemical concentration and physical property inputs and the model comprising optical sensor inputs.

Example Six

A computer-implemented method for determining a synthetic gas-oil-ratio for a gas dominant fluid, the method comprising optimizing a gas-oil-ratio database using a genetic algorithm and a multivariate regression simulator; and generating the synthetic gas-oil-ratio for the gas dominant fluid, wherein optimizing a gas-oil-ratio database using a genetic algorithm and a multivariate regression simulator comprises defining gas-oil-ratio searching boundaries gas-oil-ratio for each gas dominant fluid; generating an initial population of gas-oil-ratio data for a set of gas dominant fluids; and evaluating synthetic gas-oil-ratio assignments for the initial population using the multivariate regression simulator, wherein evaluating synthetic gas-oil-ratio assignments for the initial population using the multivariate regression simulator comprises combining the initial population of gas-oil-ratio data for a set of gas dominant fluids and a set of data for other fluids from a standard optical fluid library, wherein the step of combining forms a combined fluid set; and calculating an overall gas-oil-ratio prediction error through a plurality of models having a plurality of inputs, wherein calculating an overall gas-oil-ratio prediction error through a plurality of models having a plurality of inputs comprises calculating a cost function representing the overall gas-oil-ratio prediction error, wherein the cost function comprises a standard calibration error of gas-oil-ratio prediction for each model of the plurality of models.

Example Seven

A computer-implemented method for determining a synthetic gas-oil-ratio for a gas dominant fluid, the method comprising optimizing a gas-oil-ratio database using a genetic algorithm and a multivariate regression simulator; and generating the synthetic gas-oil-ratio for the gas dominant fluid, wherein optimizing a gas-oil-ratio database using a genetic algorithm and a multivariate regression simulator comprises defining gas-oil-ratio searching boundaries gas-oil-ratio for each gas dominant fluid; generating an initial population of gas-oil-ratio data for a set of gas dominant fluids; and evaluating synthetic gas-oil-ratio assignments for the initial population using the multivariate regression simulator, wherein evaluating synthetic gas-oil-ratio assignments for the initial population using the multivariate regression simulator comprises combining the initial population of gas-oil-ratio data for a set of gas dominant fluids and a set of data for other fluids from a standard optical fluid library, wherein the step of combining forms a combined fluid set; and calculating an overall gas-oil-ratio prediction error through a plurality of models having a plurality of inputs, wherein calculating an overall gas-oil-ratio prediction error through a plurality of models having a plurality of inputs comprises calculating a cost function representing the overall gas-oil-ratio prediction error, wherein the cost function comprises a standard calibration error of gas-oil-ratio prediction for each model of the plurality of models, wherein the standard calibration error of gas-oil-ratio prediction for each model comprises a relative error over at least one of a low gas-oil-ratio oil and water-brine mixture, a medium gas-oil-ratio and live oil condensates mixture, and a high gas-oil-ratio gas.

Example Eight

A computer-implemented method for determining a synthetic gas-oil-ratio for a gas dominant fluid, the method comprising optimizing a gas-oil-ratio database using a genetic algorithm and a multivariate regression simulator; and generating the synthetic gas-oil-ratio for the gas dominant fluid, wherein optimizing a gas-oil-ratio database using a genetic algorithm and a multivariate regression simulator comprises defining gas-oil-ratio searching boundaries gas-oil-ratio for each gas dominant fluid; generating an initial population of gas-oil-ratio data for a set of gas dominant fluids; and evaluating synthetic gas-oil-ratio assignments for the initial population using the multivariate regression simulator, wherein evaluating synthetic gas-oil-ratio assignments for the initial population using the multivariate regression simulator comprises combining the initial population of gas-oil-ratio data for a set of gas dominant fluids and a set of data for other fluids from a standard optical fluid library, wherein the step of combining forms a combined fluid set; calculating an overall gas-oil-ratio prediction error through a plurality of models having a plurality of inputs; determining whether a stop criterion for the overall gas-oil-ratio prediction error is met; and applying the genetic algorithm based on the overall gas-oil-ratio prediction error until the stop criterion is met.

Example Nine

A computer-implemented method for determining a synthetic gas-oil-ratio for a gas dominant fluid, the method comprising optimizing a gas-oil-ratio database using a genetic algorithm and a multivariate regression simulator; and generating the synthetic gas-oil-ratio for the gas dominant fluid, wherein optimizing a gas-oil-ratio database using a genetic algorithm and a multivariate regression simulator comprises defining gas-oil-ratio searching boundaries gas-oil-ratio for each gas dominant fluid; generating an initial population of gas-oil-ratio data for a set of gas dominant fluids; and evaluating synthetic gas-oil-ratio assignments for the initial population using the multivariate regression simulator, wherein evaluating synthetic gas-oil-ratio assignments for the initial population using the multivariate regression simulator comprises combining the initial population of gas-oil-ratio data for a set of gas dominant fluids and a set of data for other fluids from a standard optical fluid library, wherein the step of combining forms a combined fluid set; calculating an overall gas-oil-ratio prediction error through a plurality of models having a plurality of inputs; determining whether a stop criterion for the overall gas-oil-ratio prediction error is met; and applying the genetic algorithm based on the overall gas-oil-ratio prediction error until the stop criterion is met, wherein applying the genetic algorithm based on the overall gas-oil-ratio prediction error until the stop criterion is met comprises ranking the overall gas-oil-ratio prediction error over the combined fluid samples; and updating the gas-oil-ratio assigned for each gas dominant fluid using at least one of selection, crossover, and mutation method genetic operators through multiple generations of calculations to determine whether the stop criterion is met.

Example Ten

A computer-implemented method for determining a synthetic gas-oil-ratio for a gas dominant fluid, the method comprising optimizing a gas-oil-ratio database using a genetic algorithm and a multivariate regression simulator; and generating the synthetic gas-oil-ratio for the gas dominant fluid, wherein optimizing a gas-oil-ratio database using a genetic algorithm and a multivariate regression simulator comprises defining gas-oil-ratio searching boundaries gas-oil-ratio for each gas dominant fluid; generating an initial population of gas-oil-ratio data for a set of gas dominant fluids; and evaluating synthetic gas-oil-ratio assignments for the initial population using the multivariate regression simulator, wherein evaluating synthetic gas-oil-ratio assignments for the initial population using the multivariate regression simulator comprises combining the initial population of gas-oil-ratio data for a set of gas dominant fluids and a set of data for other fluids from a standard optical fluid library, wherein the step of combining forms a combined fluid set; and calculating an overall gas-oil-ratio prediction error through a plurality of models having a plurality of inputs, wherein calculating an overall gas-oil-ratio prediction error through a plurality of models having a plurality of inputs comprises calculating a cost function representing the overall gas-oil-ratio prediction error using an equation:

$$F = L_1 \times SEC_1 + L_2 \times SEC_2 + L_3 \times SEC_3$$

wherein F is the cost function, $L_1$, $L_2$ and $L_3$ are weighting coefficients, $SEC_1$ is a standard error of calibration for a gas-oil-ratio prediction calculated with a model comprising fluid chemical concentrations and physical properties inputs; $SEC_2$ is a standard error of calibration for a gas-oil-ratio prediction calculated with a model comprising optical sensor responses inputs; and $SEC_3$ is a standard error of calibration for a gas-oil-ratio prediction calculated with the model comprising a combination of the model comprising fluid chemical concentrations and physical properties inputs and the model comprising optical sensor inputs.

Example Eleven

A computer-implemented method for determining a synthetic gas-oil-ratio for a gas dominant fluid, the method comprising optimizing a gas-oil-ratio database using a genetic algorithm and a multivariate regression simulator; generating the synthetic gas-oil-ratio for the gas dominant fluid; and recalibrating a universal gas-oil-ratio predictive model using a neural networks algorithm to include tool-specific inputs.

Example Twelve

A system comprising at least one processor; at least one memory coupled to the at least one processor and storing instructions that when executed by the at least one processor performs operations comprising optimizing a gas-oil-ratio database using a genetic algorithm and a multivariate regression simulator; and generating a synthetic gas-oil-ratio for a gas dominant fluid.

Example Thirteen

A system comprising at least one processor; at least one memory coupled to the at least one processor and storing instructions that when executed by the at least one processor performs operations comprising optimizing a gas-oil-ratio database using a genetic algorithm and a multivariate regression simulator; and generating a synthetic gas-oil-ratio for a gas dominant fluid, wherein the operations for optimizing a gas-oil-ratio database using a genetic algorithm and a multivariate regression simulator comprises defining gas-oil-ratio searching boundaries gas-oil-ratio for each gas dominant fluid; assigning randomly a synthetic gas-oil-ratio for each gas dominant fluid in a set of gas dominant fluids in the initial population of gas-oil-ratio data, wherein the gas-oil-ratio for each gas dominant fluid is within the searching boundaries; generating an initial population of gas-oil-ratio data for a set of gas dominant fluids; and evaluating synthetic gas-oil-ratio assignments for the initial population using the multivariate regression simulator.

Example Fourteen

A system comprising at least one processor; at least one memory coupled to the at least one processor and storing instructions that when executed by the at least one processor performs operations comprising optimizing a gas-oil-ratio database using a genetic algorithm and a multivariate regression simulator; and generating a synthetic gas-oil-ratio for a gas dominant fluid, wherein the operations for optimizing a gas-oil-ratio database using a genetic algorithm and a multivariate regression simulator comprises defining gas-oil-ratio searching boundaries gas-oil-ratio for each gas dominant fluid; assigning randomly a synthetic gas-oil-ratio for each gas dominant fluid in a set of gas dominant fluids in the initial population of gas-oil-ratio data, wherein the gas-oil-ratio for each gas dominant fluid is within the searching boundaries; generating an initial population of gas-oil-ratio data for a set of gas dominant fluids; and evaluating synthetic gas-oil-ratio assignments for the initial population using the multivariate regression simulator, wherein the operations for evaluating synthetic gas-oil-ratio assignments for the initial population using the multivariate regression simulator comprises combining the initial population of gas-oil-ratio data for a set of gas dominant fluids and a set of data for other fluids from a standard optical fluid library, wherein the step of combining forms a combined fluid set; calculating an overall gas-oil-ratio prediction error through a plurality of models having a plurality of inputs; determining whether a stop criterion for the overall gas-oil-ratio prediction error is met; and applying the genetic algorithm based on the overall gas-oil-ratio prediction error until the stop criterion is met.

Example Fifteen

A system comprising at least one processor; at least one memory coupled to the at least one processor and storing instructions that when executed by the at least one processor performs operations comprising optimizing a gas-oil-ratio database using a genetic algorithm and a multivariate regression simulator; and generating a synthetic gas-oil-ratio for a gas dominant fluid, wherein the operations for optimizing a gas-oil-ratio database using a genetic algorithm and a multivariate regression simulator comprises defining gas-oil-ratio searching boundaries gas-oil-ratio for each gas dominant fluid; assigning randomly a synthetic gas-oil-ratio for each gas dominant fluid in a set of gas dominant fluids in the initial population of gas-oil-ratio data, wherein the gas-oil-ratio for each gas dominant fluid is within the searching boundaries; generating an initial population of gas-oil-ratio data for a set of gas dominant fluids; and evaluating synthetic gas-oil-ratio assignments for the initial population using the multivariate regression simulator, wherein the operations for evaluating synthetic gas-oil-ratio assignments for the initial population using the multivariate regression simulator comprises combining the initial population of gas-oil-ratio data for a set of gas dominant fluids and a set of data for other fluids from a standard optical fluid library, wherein the step of combining forms a combined fluid set; calculating an overall gas-oil-ratio prediction error through a plurality of models having a plurality of inputs; determining whether a stop criterion for the overall gas-oil-ratio prediction error is met; and applying the genetic algorithm based on the overall gas-oil-ratio prediction error until the stop criterion is met; wherein the operations applying the genetic algorithm based on the overall gas-oil-ratio prediction error until the stop criterion is met comprises ranking the overall gas-oil-ratio prediction error over the combined fluid samples; and updating the gas-oil-ratio assigned for each gas dominant fluid using at least one of selection, crossover, and mutation method genetic operators through multiple generations of calculations to determine whether the stop criterion is met.

Example Sixteen

A system comprising at least one processor; at least one memory coupled to the at least one processor and storing instructions that when executed by the at least one processor performs operations comprising optimizing a gas-oil-ratio database using a genetic algorithm and a multivariate regression simulator; and generating a synthetic gas-oil-ratio for a gas dominant fluid, wherein the at least one memory coupled to the at least one processor and storing instructions that when executed by the at least one processor performs operations further comprises recalibrating a universal gas-oil-ratio predictive model using a neural networks algorithm to include tool-specific inputs.

Example Seventeen

A non-transitory computer readable medium comprising computer executable instructions for determining a synthetic gas-oil-ratio for a gas dominant fluid, the computer executable instructions when executed causes one or more machines to perform operations comprising optimizing a gas-oil-ratio database using a genetic algorithm and a multivariate regression simulator; and generating the synthetic gas-oil-ratio for the gas dominant fluid.

Example Eighteen

A non-transitory computer readable medium comprising computer executable instructions for determining a synthetic gas-oil-ratio for a gas dominant fluid, the computer executable instructions when executed causes one or more machines to perform operations comprising optimizing a gas-oil-ratio database using a genetic algorithm and a multivariate regression simulator; and generating the synthetic gas-oil-ratio for the gas dominant fluid, wherein the operations for optimizing a gas-oil-ratio database using a genetic algorithm and a multivariate regression simulator comprises defining gas-oil-ratio searching boundaries gas-oil-ratio for each gas dominant fluid; assigning randomly a synthetic gas-oil-ratio for each gas dominant fluid in a set of gas dominant fluids in the initial population of gas-oil-ratio data, wherein the gas-oil-ratio for each gas dominant fluid is within the searching boundaries; generating an initial population of gas-oil-ratio data for a set of gas dominant fluids; and evaluating synthetic gas-oil-ratio assignments for the initial population using the multivariate regression simulator.

Example Nineteen

A non-transitory computer readable medium comprising computer executable instructions for determining a synthetic gas-oil-ratio for a gas dominant fluid, the computer executable instructions when executed causes one or more machines to perform operations comprising optimizing a gas-oil-ratio database using a genetic algorithm and a multivariate regression simulator; and generating the synthetic gas-oil-ratio for the gas dominant fluid, wherein the operations for optimizing a gas-oil-ratio database using a genetic algorithm and a multivariate regression simulator comprises defining gas-oil-ratio searching boundaries gas-oil-ratio for each gas dominant fluid; assigning randomly a synthetic gas-oil-ratio for each gas dominant fluid in a set of gas dominant fluids in the initial population of gas-oil-ratio data, wherein the gas-oil-ratio for each gas dominant fluid is within the searching boundaries; generating an initial population of gas-oil-ratio data for a set of gas dominant fluids; and evaluating synthetic gas-oil-ratio assignments for the initial population using the multivariate regression simulator, wherein the operations for evaluating synthetic gas-oil-ratio assignments for the initial population using the multivariate regression simulator comprises combining the initial population of gas-oil-ratio data for a set of gas dominant fluids and a set of data for other fluids from a standard optical fluid library, wherein the step of combining forms a combined fluid set, calculating an overall gas-oil-ratio prediction error through a plurality of models having a plurality of inputs; determining whether a stop criterion for the overall gas-oil-ratio prediction error is met; and applying the genetic algorithm based on the overall gas-oil-ratio prediction error until the stop criterion is met.

Example Twenty

A non-transitory computer readable medium comprising computer executable instructions for determining a synthetic gas-oil-ratio for a gas dominant fluid, the computer executable instructions when executed causes one or more machines to perform operations comprising optimizing a gas-oil-ratio database using a genetic algorithm and a multivariate regression simulator; and generating the synthetic gas-oil-ratio for the gas dominant fluid, wherein the computer executable instructions when executed causes one or more machines to perform operations further comprises recalibrating a universal gas-oil-ratio predictive model using a neural networks algorithm to include tool-specific inputs.

Example Twenty-One

A computer-implemented method for generating a synthetic gas-oil-ratio for a gas dominant fluid, the method comprising selecting calibration inputs for a partial-least-square gas-oil-ratio predictive model applied to a standard optical fluid database; defining gas-oil-ratio searching boundaries for each gas-dominant sample; defining initial population size and stop criterion with use of a genetic algorithm; creating an initial population of gas-dominant gas-oil-ratio data under the constraints for each searching boundary; assigning randomly a gas-oil-ratio for each gas-dominant gas-oil-ratio in a set of gas dominant fluids; combining gas-dominant gas-oil-ratio data in the initial population and other fluid gas-oil-ratio in a standard optical fluid database to form complete training data sets for each calibration model; calculating a cost function representing an overall gas-oil-ratio prediction error; applying a genetic algorithm to iteratively minimize the cost function until reaching at least one of the threshold and maximum number of generations; finalizing the gas-oil-ratio assigned for each gas dominant fluid; and recalibrating the gas-oil-ratio predictive model in an updated database using tool-specific inputs with neural networks algorithm.

Example Twenty-Two

A computer-implemented method for generating a synthetic gas-oil-ratio for a gas dominant fluid, the method comprising selecting calibration inputs for a partial-least-square gas-oil-ratio predictive model applied to a standard optical fluid database; defining gas-oil-ratio searching boundaries for each gas-dominant sample; defining initial population size and stop criterion with use of a genetic algorithm; creating an initial population of gas-dominant gas-oil-ratio data under the constraints for each searching boundary; assigning randomly a gas-oil-ratio for each gas-dominant gas-oil-ratio in a set of gas dominant fluids; combining gas-dominant gas-oil-ratio data in the initial population and other fluid gas-oil-ratio in a standard optical fluid database to form complete training data sets for each calibration model; calculating a cost function representing an overall gas-oil-ratio prediction error using at least one of the following equations:

$$F = L_1 \times SEC_1 + L_2 \times SEC_2 + L_3 \times SEC_3$$

wherein F is the cost function, $L_1$, $L_2$ and $L_3$ are weighting coefficients, $SEC_1$ is a standard error of calibration for a gas-oil-ratio prediction calculated with a model comprising fluid chemical concentrations and physical properties inputs; $SEC_2$ is a standard error of calibration for a gas-oil-ratio prediction calculated with a model comprising optical sensor responses inputs; and $SEC_3$ is a standard error of calibration for a gas-oil-ratio prediction calculated with the model comprising a combination of the model comprising fluid chemical concentrations and physical properties inputs and the model comprising optical sensor inputs; and $$SEC = K_1 \frac{RMS_1 \times 2 \times 100}{MIN(GOR_1) + MAX(GOR_1)} + K_2 \frac{RMS_2 \times 2 \times 100}{MIN(GOR_2) + MAX(GOR_2)} + K_3 \frac{RMS_3 \times 2 \times 100}{MIN(GOR_3) + MAX(GOR_3)}$$

wherein $K_1$, $K_2$ and $K_3$ are weighting coefficients, $RMS_1$ and $GOR_1$, $RMS_2$ and $GOR_2$ and $RMS_3$ and $GOR_3$ are respectively root of mean-squared error and target gas-oil-ratios within each group; applying a genetic algorithm to iteratively minimize the cost function until reaching at least one of a threshold and maximum number of generations; finalizing the gas-oil-ratio assigned for each gas dominant fluid; and recalibrating the gas-oil-ratio predictive model in an updated database using tool-specific inputs with neural networks algorithm.

Example Twenty-Three

A system comprising at least one processor; at least one memory coupled to the at least one processor and storing instructions that when executed by the at least one processor performs operations comprising selecting calibration inputs for a partial-least-square gas-oil-ratio predictive model applied to a standard optical fluid database; defining gas-oil-ratio searching boundaries for each gas-dominant sample; defining initial population size and stop criterion with use of a genetic algorithm; creating an initial population of gas-dominant gas-oil-ratio data under the constraints for each searching boundary; assigning randomly a gas-oil-ratio for each gas-dominant gas-oil-ratio in a set of gas dominant fluids; combining gas-dominant gas-oil-ratio data in the initial population and other fluid gas-oil-ratio in a standard optical fluid database to form complete training data sets for each calibration model; calculating a cost function representing an overall gas-oil-ratio prediction error; applying a genetic algorithm to iteratively minimize the cost function until reaching at least one of the threshold and maximum number of generations; finalizing the gas-oil-ratio assigned for each gas dominant fluid; and recalibrating the gas-oil-ratio predictive model in an updated database using tool-specific inputs with neural networks algorithm.

Example Twenty-Four

A system comprising at least one processor; at least one memory coupled to the at least one processor and storing instructions that when executed by the at least one processor performs operations comprising selecting calibration inputs for a partial-least-square gas-oil-ratio predictive model applied to a standard optical fluid database; defining gas-oil-ratio searching boundaries for each gas-dominant sample; defining initial population size and stop criterion with use of a genetic algorithm; creating an initial population of gas-dominant gas-oil-ratio data under the constraints for each searching boundary; assigning randomly a gas-oil-ratio for each gas-dominant gas-oil-ratio in a set of gas dominant fluids; combining gas-dominant gas-oil-ratio data in the initial population and other fluid gas-oil-ratio in a standard optical fluid database to form complete training data sets for each calibration model; calculating a cost function representing an overall gas-oil-ratio prediction error using at least one of the following equations:

$$F = L_1 \times SEC_T + L_2 \times SEC_2 + L_3 \times SEC_3$$

wherein F is the cost function, $L_1$, $L_2$ and $L_3$ are weighting coefficients, $SEC_1$ is a standard error of calibration for a gas-oil-ratio prediction calculated with a model comprising fluid chemical concentrations and physical properties inputs; $SEC_2$ is a standard error of calibration for a gas-oil-ratio prediction calculated with a model comprising optical sensor responses inputs; and $SEC_3$ is a standard error of calibration for a gas-oil-ratio prediction calculated with the model comprising a combination of the model comprising fluid chemical concentrations and physical properties inputs and the model comprising optical sensor inputs; and $$SEC = K_1 \frac{RMS_1 \times 2 \times 100}{MIN(GOR_1) + MAX(GOR_1)} + K_2 \frac{RMS_2 \times 2 \times 100}{MIN(GOR_2) + MAX(GOR_2)} + K_3 \frac{RMS_3 \times 2 \times 100}{MIN(GOR_3) + MAX(GOR_3)}$$

wherein $K_1$, $K_2$ and $K_3$ are weighting coefficients, $RMS_1$ and $GOR_1$, $RMS_2$ and $GOR_2$ and $RMS_3$ and $GOR_3$ are respectively root of mean-squared error and target gas-oil-ratios within each group; applying a genetic algorithm to iteratively minimize the cost function until reaching at least one of a threshold and maximum number of generations; finalizing the gas-oil-ratio assigned for each gas dominant fluid; and recalibrating the gas-oil-ratio predictive model in an updated database using tool-specific inputs with neural networks algorithm.

Example Twenty Five. A non-transitory computer readable medium comprising computer executable instructions for generating a synthetic gas-oil-ratio for a gas dominant fluid, the computer executable instructions when executed causes one or more machines to perform operations selecting calibration inputs for a partial-least-square gas-oil-ratio predictive model applied to a standard optical fluid database; defining gas-oil-ratio searching boundaries for each gas-dominant sample; defining initial population size and stop criterion with use of a genetic algorithm; creating an initial population of gas-dominant gas-oil-ratio data under the constraints for each searching boundary; assigning randomly a gas-oil-ratio for each gas-dominant gas-oil-ratio in a set of gas dominant fluids; combining gas-dominant gas-oil-ratio data in the initial population and other fluid gas-oil-ratio in a standard optical fluid database to form complete training data sets for each calibration model; calculating a cost function representing an overall gas-oil-ratio prediction error; applying a genetic algorithm to iteratively minimize the cost function until reaching at least one of the threshold and maximum number of generations; finalizing the gas-oil-ratio assigned for each gas dominant fluid; and recalibrating the gas-oil-ratio predictive model in an updated database using tool-specific inputs with neural networks algorithm.

Example Twenty-Six

A non-transitory computer readable medium comprising computer executable instructions for generating a synthetic gas-oil-ratio for a gas dominant fluid, the computer executable instructions when executed causes one or more machines to perform operations comprising selecting calibration inputs for a partial-least-square gas-oil-ratio predictive model applied to a standard optical fluid database; defining gas-oil-ratio searching boundaries for each gas-dominant sample; defining initial population size and stop criterion with use of a genetic algorithm; creating an initial population of gas-dominant gas-oil-ratio data under the constraints for each searching boundary; assigning randomly a gas-oil-ratio for each gas-dominant gas-oil-ratio in a set of gas dominant fluids; combining gas-dominant gas-oil-ratio data in the initial population and other fluid gas-oil-ratio in a standard optical fluid database to form complete training data sets for each calibration model; calculating a cost function representing an overall gas-oil-ratio prediction error using at least one of the following equations:

$$F = L_1 \times SEC_T + L_2 \times SEC_2 + L_3 \times SEC_3$$

wherein F is the cost function, $L_1$, $L_2$ and $L_3$ are weighting coefficients, $SEC_1$ is a standard error of calibration for a gas-oil-ratio prediction calculated with a model comprising fluid chemical concentrations and physical properties inputs; $SEC_2$ is a standard error of calibration for a gas-oil-ratio prediction calculated with a model comprising optical sensor responses inputs; and $SEC_3$ is a standard error of calibration for a gas-oil-ratio prediction calculated with the model comprising a combination of the model comprising fluid chemical concentrations and physical properties inputs and the model comprising optical sensor inputs; and $$SEC = K_1 \frac{RMS_1 \times 2 \times 100}{MIN(GOR_1) + MAX(GOR_1)} + K_2 \frac{RMS_2 \times 2 \times 100}{MIN(GOR_2) + MAX(GOR_2)} + K_3 \frac{RMS_3 \times 2 \times 100}{MIN(GOR_3) + MAX(GOR_3)}$$

wherein $K_1$, $K_2$ and $K_3$ are weighting coefficients, $RMS_1$ and $GOR_1$, $RMS_2$ and $GOR_2$ and $RMS_3$ and $GOR_3$ are respectively root of mean-squared error and target gas-oil-ratios within each group; applying a genetic algorithm to iteratively minimize the cost function until reaching at least one of a threshold and maximum number of generations; finalizing the gas-oil-ratio assigned for each gas dominant fluid; and recalibrating the gas-oil-ratio predictive model in an updated database using tool-specific inputs with neural networks algorithm.

Example Twenty-Seven

A computer-implemented method for applying a genetic algorithm to a synthetic gas-oil-ratio for a gas dominant fluid, the method comprising ranking a population of cost functions of gas-oil-ratio predictions for a set of fluids, wherein the population includes a realization of gas-dominant fluids; updating a gas-oil-ratio assigned for each gas dominant fluid using at least one of selection, crossover, and mutation method of genetic operators; and optimizing iteratively until a stop criterion is met.

Example Twenty-Eight

A system comprising at least one processor; at least one memory coupled to the at least one processor and storing instructions that when executed by the at least one processor performs operations comprising ranking a population of cost functions of gas-oil-ratio predictions for a set of fluids, wherein the population includes a realization of gas-dominant fluids; updating a gas-oil-ratio assigned for each gas dominant fluid using at least one of selection, crossover, and mutation method of genetic operators; and optimizing iteratively until a stop criterion is met.

Example Twenty-Nine

A non-transitory computer readable medium comprising computer executable instructions for applying a genetic algorithm to a synthetic gas-oil-ratio for a gas dominant fluid, the computer executable instructions when executed causes one or more machines to perform operations comprising ranking a population of cost functions of gas-oil-ratio predictions for a set of fluids, wherein the population includes a realization of gas-dominant fluids; updating a gas-oil-ratio assigned for each gas dominant fluid using at least one of selection, crossover, and mutation method of genetic operators; and optimizing iteratively until a stop criterion is met.

Example Thirty

A computer-implemented method for determining a synthetic gas-oil-ratio for a gas dominant fluid, the method comprising optimizing a gas-oil-ratio database using a genetic algorithm and a multivariate regression simulator; and generating the synthetic gas-oil-ratio for the gas dominant fluid, wherein optimizing a gas-oil-ratio database using a genetic algorithm and a multivariate regression simulator comprises defining calibration inputs comprising defined searching boundaries for gas fluid gas-oil-ratio; and generating an initial population of gas-oil-ratio data for a set of gas dominant fluids, wherein generating an initial population of gas-oil-ratio data for the gas dominant fluids comprises assigning a gas-oil-ratio for each gas dominant fluid in a set of gas dominant fluids, wherein the gas-oil-ratio for each gas dominant fluid is within the searching boundaries; and further comprises combining the initial population of gas-oil-ratio data and a set of data from a standard optical fluid library; generating an overall gas-oil-ratio prediction error for a plurality of models having a plurality of inputs; determining whether a stop criterion for the overall gas-oil-ratio prediction error; applying the genetic algorithm to the overall gas-oil-ratio prediction error until the stop criterion is met, wherein applying the genetic algorithm to the overall gas-oil-ratio prediction error until the stop criterion is met comprises ranking the overall gas-oil-ratio prediction error for each of the gas-oil-ratio assigned for each gas dominant fluid; and updating the gas-oil-ratio assigned for each gas dominant fluid using at least one of selection, crossover, and mutation method genetic operators through multiple generations of calculations to determine whether the stop criterion is met, wherein the stop criterion is at least one of a threshold and a maximum number of generations.

Example Thirty-One

A system comprising at least one processor; at least one memory coupled to the at least one processor and storing instructions that when executed by the at least one processor performs operations comprising optimizing a gas-oil-ratio database using a genetic algorithm and a multivariate regression simulator; and generating a synthetic gas-oil-ratio for a gas dominant fluid, wherein optimizing a gas-oil-ratio database using a genetic algorithm and a multivariate regression simulator comprises defining calibration inputs comprising defined searching boundaries for gas fluid gas-oil-ratio; and generating an initial population of gas-oil-ratio data for a set of gas dominant fluids, wherein generating an initial population of gas-oil-ratio data for the gas dominant fluids comprises assigning a gas-oil-ratio for each gas dominant fluid in a set of gas dominant fluids, wherein the gas-oil-ratio for each gas dominant fluid is within the searching boundaries; and further comprises combining the initial population of gas-oil-ratio data and a set of data from a standard optical fluid library; generating an overall gas-oil-ratio prediction error for a plurality of models having a plurality of inputs; determining whether a stop criterion for the overall gas-oil-ratio prediction error; applying the genetic algorithm to the overall gas-oil-ratio prediction error until the stop criterion is met, wherein applying the genetic algorithm to the overall gas-oil-ratio prediction error until the stop criterion is met comprises ranking the overall gas-oil-ratio prediction error for each of the gas-oil-ratio assigned for each gas dominant fluid; and updating the gas-oil-ratio assigned for each gas dominant fluid using at least one of selection, crossover, and mutation method genetic operators through multiple generations of calculations to determine whether the stop criterion is met, wherein the stop criterion is at least one of a threshold and a maximum number of generations.

Example Thirty-Two

A non-transitory computer readable medium comprising computer executable instructions for determining a synthetic gas-oil-ratio for a gas dominant fluid, the computer executable instructions when executed causes one or more machines to perform operations comprising optimizing a gas-oil-ratio database using a genetic algorithm and a multivariate regression simulator; and generating the synthetic gas-oil-ratio for the gas dominant fluid, wherein optimizing a gas-oil-ratio database using a genetic algorithm and a multivariate regression simulator comprises defining calibration inputs comprising defined searching boundaries for gas fluid gas-oil-ratio; and generating an initial population of gas-oil-ratio data for a set of gas dominant fluids, wherein generating an initial population of gas-oil-ratio data for the gas dominant fluids comprises assigning a gas-oil-ratio for each gas dominant fluid in a set of gas dominant fluids, wherein the gas-oil-ratio for each gas dominant fluid is within the searching boundaries; and further comprises combining the initial population of gas-oil-ratio data and a set of data from a standard optical fluid library; generating an overall gas-oil-ratio prediction error for a plurality of models having a plurality of inputs; determining whether a stop criterion for the overall gas-oil-ratio prediction error; applying the genetic algorithm to the overall gas-oil-ratio prediction error until the stop criterion is met, wherein applying the genetic algorithm to the overall gas-oil-ratio prediction error until the stop criterion is met comprises ranking the overall gas-oil-ratio prediction error for each of the gas-oil-ratio assigned for each gas dominant fluid; and updating the gas-oil-ratio assigned for each gas dominant fluid using at least one of selection, crossover, and mutation method genetic operators through multiple generations of calculations to determine whether the stop criterion is met, wherein the stop criterion is at least one of a threshold and a maximum number of generations.

While many specific example embodiments are described above, the above examples are not intended to be exhaustive or limit the invention in the form disclosed. Many modifications and variations will be apparent to those of ordinary skill in the art without departing from the scope and spirit of the invention. The scope of the claims is intended to broadly cover the disclosed embodiments and any such modifications.

The invention claimed is:

1. A computer-implemented method for determining a synthetic gas-oil-ratio for a gas dominant fluid, the method comprising:
   optimizing a gas-oil-ratio database using a genetic algorithm and a multivariate regression simulator; and
   generating the synthetic gas-oil-ratio for the gas dominant fluid.

2. The method of claim 1, wherein optimizing a gas-oil-ratio database using a genetic algorithm and a multivariate regression simulator comprises:
   defining gas-oil-ratio searching boundaries gas-oil-ratio for each gas dominant fluid;
   generating an initial population of gas-oil-ratio data for a set of gas dominant fluids; and
   evaluating synthetic gas-oil-ratio assignments for the initial population using the multivariate regression simulator.

3. The method of claim 2, wherein generating an initial population of gas-oil-ratio data for the gas dominant fluids comprises:
   assigning randomly a synthetic gas-oil-ratio for each gas dominant fluid in a set of gas dominant fluids in the initial population of gas-oil-ratio data, wherein the gas-oil-ratio for each gas dominant fluid is within the searching boundaries.

4. The method of claim 2, wherein evaluating synthetic gas-oil-ratio assignments for the initial population using the multivariate regression simulator comprises:
   combining the initial population of gas-oil-ratio data for a set of gas dominant fluids and a set of data for other fluids from a standard optical fluid library, wherein the step of combining forms a combined fluid set; and
   calculating an overall gas-oil-ratio prediction error through a plurality of models having a plurality of inputs.

5. The method of claim 4, wherein the plurality of models comprises at least one of a model comprising fluid chemical concentrations and physical property inputs, a model comprising optical sensor inputs, and a model comprising a combination of the model comprising fluid chemical concentration and physical property inputs and the model comprising optical sensor inputs.

6. The method of claim 4, wherein calculating an overall gas-oil-ratio prediction error through a plurality of models having a plurality of inputs comprises:
   calculating a cost function representing the overall gas-oil-ratio prediction error, wherein the cost function comprises a standard calibration error of gas-oil-ratio prediction for each model of the plurality of models.

7. The method of claim 6, wherein the standard calibration error of gas-oil-ratio prediction for each model comprises a relative error over at least one of a low gas-oil-ratio oil and water-brine mixture, a medium gas-oil-ratio and live oil condensates mixture, and a high gas-oil-ratio gas.

8. The method of claim 4, further comprising:
   determining whether a stop criterion for the overall gas-oil-ratio prediction error is met; and
   applying the genetic algorithm based on the overall gas-oil-ratio prediction error until the stop criterion is met.

9. The method of claim 8, wherein applying the genetic algorithm based on the overall gas-oil-ratio prediction error until the stop criterion is met comprises:
   ranking the overall gas-oil-ratio prediction error over the combined fluid samples; and
   updating the gas-oil-ratio assigned for each gas dominant fluid using at least one of selection, crossover, and mutation method genetic operators through multiple generations of calculations to determine whether the stop criterion is met.

10. The method of claim 4, wherein calculating an overall gas-oil-ratio prediction error through a plurality of models having a plurality of inputs comprises:
    calculating a cost function representing the overall gas-oil-ratio prediction error using an equation:

$$F = L_1 \times SEC_1 + L_2 \times SEC_2 + L_3 \times SEC_3$$

wherein F is the cost function, $L_1$, $L_2$ and $L_3$ are weighting coefficients, $SEC_1$ is a standard error of calibration for a gas-oil-ratio prediction calculated with a model comprising fluid chemical concentrations and physical properties inputs; $SEC_2$ is a standard error of calibration for a gas-oil-ratio prediction calculated with a model comprising optical sensor responses inputs; and $SEC_3$ is a standard error of calibration for a gas-oil-ratio prediction calculated with the model comprising a combination of the model comprising fluid chemical concentrations and physical properties inputs and the model comprising optical sensor inputs.

11. The method of claim 1, further comprising:
    recalibrating a universal gas-oil-ratio predictive model using a neural networks algorithm to include tool-specific inputs.

12. A system comprising:
    at least one processor;
    at least one memory coupled to the at least one processor and storing instructions that when executed by the at least one processor performs operations comprising:
        optimizing a gas-oil-ratio database using a genetic algorithm and a multivariate regression simulator; and
        generating a synthetic gas-oil-ratio for a gas dominant fluid.

13. The system of claim 12, wherein the operations for optimizing a gas-oil-ratio database using a genetic algorithm and a multivariate regression simulator comprises:
    defining gas-oil-ratio searching boundaries gas-oil-ratio for each gas dominant fluid;
    generating an initial population of gas-oil-ratio data for a set of gas dominant fluids;
    assigning randomly a synthetic gas-oil-ratio for each gas dominant fluid in a set of gas dominant fluids in the initial population of gas-oil-ratio data, wherein the gas-oil-ratio for each gas dominant fluid is within the searching boundaries; and
    evaluating synthetic gas-oil-ratio assignments for the initial population using the multivariate regression simulator.

14. The system of claim 13, wherein the operations for evaluating synthetic gas-oil-ratio assignments for the initial population using the multivariate regression simulator comprises:

combining the initial population of gas-oil-ratio data for a set of gas dominant fluids and a set of data for other fluids from a standard optical fluid library, wherein the step of combining forms a combined fluid set;

calculating an overall gas-oil-ratio prediction error through a plurality of models having a plurality of inputs;

determining whether a stop criterion for the overall gas-oil-ratio prediction error is met; and applying the genetic algorithm based on the overall gas-oil-ratio prediction error until the stop criterion is met.

15. The system of claim 14, wherein the operations applying the genetic algorithm based on the overall gas-oil-ratio prediction error until the stop criterion is met comprises:

ranking the overall gas-oil-ratio prediction error over the combined fluid samples; and updating the gas-oil-ratio assigned for each gas dominant fluid using at least one of selection, crossover, and mutation method genetic operators through multiple generations of calculations to determine whether the stop criterion is met.

16. The system of claim 12, wherein the at least one memory coupled to the at least one processor and storing instructions that when executed by the at least one processor performs operations further comprises:

recalibrating a universal gas-oil-ratio predictive model using a neural networks algorithm to include tool-specific inputs.

17. A non-transitory computer readable medium comprising computer executable instructions for determining a synthetic gas-oil-ratio for a gas dominant fluid, the computer executable instructions when executed causes one or more machines to perform operations comprising:

optimizing a gas-oil-ratio database using a genetic algorithm and a multivariate regression simulator; and generating the synthetic gas-oil-ratio for the gas dominant fluid.

18. The non-transitory computer readable medium of claim 17, wherein the operations for optimizing a gas-oil-ratio database using a genetic algorithm and a multivariate regression simulator comprises:

defining gas-oil-ratio searching boundaries gas-oil-ratio for each gas dominant fluid;

generating an initial population of gas-oil-ratio data for a set of gas dominant fluids;

assigning randomly a synthetic gas-oil-ratio for each gas dominant fluid in a set of gas dominant fluids in the initial population of gas-oil-ratio data, wherein the gas-oil-ratio for each gas dominant fluid is within the searching boundaries; and evaluating synthetic gas-oil-ratio assignments for the initial population using the multivariate regression simulator.

19. The non-transitory computer readable medium of claim 18, wherein the operations for evaluating synthetic gas-oil-ratio assignments for the initial population using the multivariate regression simulator comprises:

combining the initial population of gas-oil-ratio data for a set of gas dominant fluids and a set of data for other fluids from a standard optical fluid library, wherein the step of combining forms a combined fluid set;

calculating an overall gas-oil-ratio prediction error through a plurality of models having a plurality of inputs;

determining whether a stop criterion for the overall gas-oil-ratio prediction error is met; and applying the genetic algorithm based on the overall gas-oil-ratio prediction error until the stop criterion is met.

20. The non-transitory computer readable medium of claim 17, wherein the computer executable instructions when executed causes one or more machines to perform operations further comprises:

recalibrating a universal gas-oil-ratio predictive model using a neural networks algorithm to include tool-specific inputs.

* * * * *